US006451305B1

(12) United States Patent
Boussiotis et al.

(10) Patent No.: US 6,451,305 B1
(45) Date of Patent: *Sep. 17, 2002

(54) METHODS FOR STIMULATING T CELL RESPONSES TO TUMOR CELLS EXPRESSING LFA-3 AND A CD28 OR CTLA4 LIGAND

(75) Inventors: Vassiliki A. Boussiotis; Gordon J. Freeman, both of Brookline; Lee M. Nadler, Newton, all of MA (US)

(73) Assignee: Dana-Farber Cancer Institute (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/457,483

(22) Filed: Jun. 1, 1995

Related U.S. Application Data

(63) Continuation-in-part of application No. 08/207,932, filed on Mar. 8, 1994, and a continuation-in-part of application No. PCT/US95/02916, filed on Mar. 8, 1995.

(51) Int. Cl.[7] .......................... A61K 48/00; C12N 5/10

(52) U.S. Cl. ................. 424/93.21; 424/93.2; 424/93.7; 435/325; 435/365.1; 435/440; 435/455

(58) Field of Search ............................ 424/93.2, 93.21; 435/325, 365.1, 440

(56) References Cited

U.S. PATENT DOCUMENTS

| 5,116,964 A | | 5/1992 | Capon et al. ................. 536/27 |
|---|---|---|---|
| 5,188,955 A | * | 2/1993 | Haberman |
| 5,434,131 A | | 7/1995 | Linsley et al. ................. 514/2 |
| 5,858,776 A | * | 1/1999 | Ostrand-Rosenberg et al. |
| 5,942,607 A | * | 8/1999 | Freeman et al. |

FOREIGN PATENT DOCUMENTS

| EP | 0503646 A1 | 12/1992 |
|---|---|---|
| WO | WO 90/05541 | 5/1990 |
| WO | WO 91/11194 | 8/1991 |
| WO | WO 92/00092 | 1/1992 |
| WO | WO 92/15671 | 9/1992 |
| WO | WO 93/00431 | 1/1993 |
| WO | WO 93/06852 | 4/1993 |
| WO | WO 93/06866 | 4/1993 |

OTHER PUBLICATIONS

1. De Waal et al. J. Immunol. 150: 4754–4765, 1993.*
1. Martin–Foutecha et al. Eur. J. Immunol. 26: 1851–1859 (1996).*
2. Leong et al. Int. J. Cancer 71: 476–482 (1997).*
1. Baskar et al. PNAS 90: 5687–5690 (1980).*
2. Townsend et al. Science 259: 368–370 (1993).*
3. Chen et al. Cell 71: 1093–1102 (1992).*
4. Chen et al. Immunol. Today 14: 483–486 (1993).*
5. Gilboa Sem. On Cology 23: 101–107 (1996).*
6. Dermer Biotechnology 12: 320 (1994).*
7. Osband Immunol. Today 11: 193–195 (1990).*
8. Boon Int. J. Cancer 54: 177–180 (1993).*
9. Boon Adv. Cancer Res. 58: 177–210 (1992).*

Azuma, M., et al., "B70 Antigen is a Second Ligand for CTLA–4 and CD28," *Nature*, vol. 366, 76–79 (1993).
Bell, G. and Imboden, J., "CD2 and the Regulation of T Cell Anergy," *The Journal of Immunology*, 2805–2807 (1995).
Beverly, B., et al., "Reversal of in Vitro T Cell Clonal Anergy by IL–2 Stimulation," *International Immunology*, vol. 4, No. 6, 661–671 (1992).
Bierer, B., et al., "Interaction of CD2 with its Ligand, LFA–3, in Human T Cell Proliferation," *The Journal of Immunology*, vol. 140, No. 10, 3358–3363 (1988).
Bierer, B., et al., "Synergistic T Cell Activation Via the Physiological Ligands for CD2 and the T Cell Receptor," *J. Exp. Med.*, vol. 168, 1145–1156 (1988).
Boussiotis, V., et al., "B7 but not Intercellular Adhesion Molecule–1 Costimulation Prevents the Induction of Human Alloantigen–specific Tolerance," *J. Exp. Med.*, vol. 178, 1753–1763 (1993).
Boussiotis, V., et al., "CD2 is Involved in Maintenance and Reversal of Human Alloantigen–specific Clonal Anergy," *J. Exp. Med.*, vol. 180, 1665–1673 (1994).
Boussiotis, V., et al., "Human Alloantigen Specific Clonal Anergy to Lymphoblastoid Cells is Reversed Following Culture with IL–2 or IL–4," *Blood*, vol. 82, 304A (1993).
Brottier, P., et al., "T Cell Activation Via CD2 [T, gp50] Molecules: Accessory Cells are Required to Trigger T Cell Activation Via CD2–D66 Plus CD2–9.6/T11$_1$ Epitopes," *The Journal of Immunology*, vol. 135, No. 3, 1624–1631 (1985).
Dustin, M., et al., "Anchoring Mechanisms for LFA–3 Cell Adhesion Glycoprotein at Membrane Surface," *Nature*, vol. 329, 846–848 (1987).
Freedman, A., et al., "B7, a B Cell–Restricted Antigen that Identifies Preactivated B Cells," Division of Tumor Immunology, Dana–Farber Cancer Institute and the Department of Medicine. The Journal of Immunology 3260–3267 (1987).
Freeman, G., et al., "B7, a new Member of the Ig Superfamily with Unique Expression on Activated and Neoplastic B Cells," *The Journal of Immunology*, vol. 143, No. 8, 2714–2722 (1989).
Freeman, G., et al., "Cloning of B7–2: A CTLA–4 Counter–Receptor that Costimulates Human T Cell Proliferation." *Science*, vol. 262, 909–911 (1993).
Freeman, G., et al., "Murine B7–2, an Alternative CTLA4 Counter–receptor that Costimulates T Cell Proliferation and Interleukin 2 Production." *The Journal of Experimental Medicine*, vol. 178, 2185–2192 (1993).

(List continued on next page.)

Primary Examiner—Phillip Gambel
(74) Attorney, Agent, or Firm—Lahive & Cockfield, LLP; Amy E. Mandragouras, Esq.; DeAnn F. Smith, Esq.

(57) ABSTRACT

Methods for stimulating a T cell response to a tumor cell in a subject with a tumor which involve modifying the tumor cell to express a CD2 ligand and a CD28 or CTLA4 ligand, are disclosed. Methods wherein the tumor cell is obtained from the subject and modified ex vivo to form a modified tumor cell and then the modified tumor cell is administered to the subject, are also disclosed.

12 Claims, 7 Drawing Sheets

OTHER PUBLICATIONS

Freeman, G., et al., "Structure, Expression, and T Cell Costimulatory Activity of the Murine Homologue of the Human B Lymphocyte Activation Antigen B7," *J. Exp. Med.*, vol. 174, 625–631 (1991).

Freeman, G., et al., "Uncovering of Functional Alternative CTLA–4 Counter–Receptor in B7–Deficient Mice," *Science*, vol. 262, 907–909 (1993).

Gimmi, C., et al., "B–cell Surface Antigen B7 Provides a Costimulatory Signal that Induces T Cells to Proliferate and Secrete Interleukin 2," *Proc. Natl. Acad. Sci. USA*, vol. 88, 6575–6579 (1991).

Gimmi, C., et al., "Human T–cell Clonal Anergy is Induced by Antigen Presentation in the Absence of B7 Costimulation," *Proc. Natl. Acad. Sci. USA*, vol. 90, 6586–6590 (1993).

Harding, F., et al., "CD28–mediated Signaling Co–stimulates Murine T Cells and Prevents Induction of Anergy in T–cell Clones," *Nature*, vol. 356, 607–609 (1992).

Hathcock, K., et al., "Identification of an Alternative CTLA–4 Ligand Costimulatory for T Cell Activation," *Science*, vol. 262, 905–907 (1993).

Koyasu, S., et al., "Role of Interaction of CD2 Molecules with Lymphocyte Function–associated Antigen 3 in T–cell Recognition of Nominal Antigen," *Proc. Natl. Acad. Sci. USA*, vol. 87, 2603–2607 (1990).

Lenschow, D., et al., "Long–Term Survival of Xenogeneic Pancreatic Islet Grafts Induced by CTLA4Ig," *Science*, vol. 257, 789–791 (1992).

Lin, H., et al., "Long–Term Acceptance of Major Histocompatibility Complex Mismatched Cardiac Allografts Induced by CTLA4Ig Plus Donor–specific Transfusion," *J. Exp. Med.*, vol. 178, 1801–1806 (1993).

Linsley, P., et al., "Binding of the B Cell Activitation Antigen B7 to CD28 Costimulates T Cell Proliferation and Interleukin 2 mRNA Accumulation," *J. Exp. Med.*, vol. 173, 721–730 (1991).

Linsley, P., et al., "Immunosuppression in Vivo by a Soluble Form of the CTLA–4 T Cell Activation Molecule," *Science*, vol. 257, 792–795 (1992).

Meuer, S., et al., "An Alternative Pathway of T–Cell Activation: A Functional Role for the 50 kd T11 Sheep Erythrocyte Receptor Protein," *Cell*, vol. 36, 897–906 (1984).

Moingeon, P., et al., "CD2–mediated Adhesion Facilitates T Lymphocyte Antigen Recognition Function," *Nature*, vol. 339, 312–314 (1989).

Pepinsky, R., et al., "The Increased Potency of Cross–linked Lymphocyte Function–associated Antigen–3 (LFA–3) Multimers is a Direct Consequence of Changes in Valency," *The Journal of Biological Chemistry*, vol. 266, No. 27, 18244–18249 (1991).

Seed, B., "An LFA–3 cDNA Encodes a Phospholipid–linked Membrane Protein Homologous to its Receptor CD2," *Nature*, vol. 329, 840–842 (1987).

Selvaraj, P., et al., "The T Lymphocyte Glycoprotein CD2 Binds the Cell Surface Ligand LFA–3," *Nature*, vol. 326, 400–403 (1987).

Tan, P., et al., "Induction of Alloantigen–specific Hyporesponsiveness in Human T Lymphocytes by Blocking Interaction of CD28 with its Natural Ligand B7/BB1," *J. Exp. Med.*, vol. 177, 165–173 (1993).

Van Gool, S., et al., "The Combination of Anti–B7 Monoclonal Antibody and Cyclosporin A Induces Alloantigen–specific Anergy During a Primary Mixed Lymphocyte Reaction," *J. Exp. Med.*, vol. 179, 715–720 (1994).

Wallner, B., et al., "Primary Structure of Lymphocyte Function–Associated Antigen 3 (LFA–3) The Ligand of the T Lymphocyte CD2 Glycoprotein," *Journal of Experimental Medicine*, vol. 166, 923–932 (1987).

Yang, S., et al., "A Common Pathway for T Lymphocyte Activation Involving Both the CD3–Ti Complex and CD2 Sheep Erythrocyte Receptor Determinants," *The Journal of Immunology*, vol. 137, No. 4, 1097–1100 (1986).

* cited by examiner

METHODS FOR STIMULATING T CELL RESPONSES TO TUMOR CELLS EXPRESSING LFA-3 AND A CD28 OR CTLA4 LIGAND

RELATED APPLICATIONS

This application is a continuation in-part of U.S. application Ser. No. 08/207,932, filed Mar. 8, 1994, entitled "Methods for Modulating T Cell Unresponsiveness" and is a continuation-in-part of International Application Ser. No. PCT/US95/02916, filed Mar. 8, 1995. The contents of these applications is incorporated herein by reference.

GOVERNMENT FUNDING

Work described herein was supported under grants CA40216 and PO1AI35225 awarded by the National Institutes of Health. The U.S. government therefore may have certain rights in this invention.

BACKGROUND OF THE INVENTION

Antigen-specific T cell responses require multiple interactions between cell surface receptors on T cells and ligands on antigen presenting cells. The primary interaction is between the T cell receptor/CD3 complex and a major histocompatibility complex molecule, which presents an antigenic peptide to the T cell receptor, thereby triggering an antigen-specific signal in the T cells. In addition to this antigen specific signal, T cell responses require a second, costimulatory signal. A costimulatory signal can be generated in T cells by stimulation of T cells through a cell surface receptor CD28 (Harding, F. A. (1992) *Nature* 356:607–609). Ligands for CD28 have been identified on antigen presenting cells (APCs). CD28 ligands include members of the B7 family of proteins, such as B7-1 and B7-2 (Freedman, A. S. et al. (1987) *J. Immunol.* 137:3260–3267; Freeman, G. J. et al. (1989) *J Immunol.* 143:2714–2722; Freeman, G. J. et al. (1991) *J. Exp. Med.* 174:625–631; Freeman, G. J. et al. (1993) *Science* 262:909–911; Azuma, M. et al. (1993) *Nature* 366:76–79; Freeman, G. J. et al. (1993) *J. Exp. Med.* 178:2185–2192). The B7 proteins have also been shown to bind another surface receptor on T cells related to CD28, termed CTLA4, although the role of CTLA4 in costimulation is still unclear (Linsley, P. S. (1991) *J. Exp. Med.* 174:561–569).

It has been demonstrated that delivery of an antigen-specific signal to a T cell in the absence of a costimulatory signal does not induce a T cell response, but rather induces a state of unresponsiveness, also termed T cell anergy (see Schwartz, R. H. (1990) *Science* 248:1349; Jenkins, M. K. et al. (1988) *J. Immunol.* 140:3324). Based upon this phenomenon, therapeutic approaches for inducing T cell unresponsiveness to an antigen have been proposed which involve the blocking of a costimulatory signal in T cells. For example, a CTLA4Ig fusion protein, which binds to both B7-1 and B7-2 and blocks their interaction with CD28, has been used to inhibit rejection of allogeneic and xenogeneic grafts (see e.g., Turka, L. A. et al. (1992) *Proc. Natl. Acad. Sci. USA* 89:11102–11105; Lenschow, D. J. et al. (1992) *Science* 257:789–792). Alternatively, therapeutic approaches have also been proposed for stimulating a T cell response to an antigen on a cell (e.g., a tumor cell). For example, tumor cells modified to express the CD28 ligand B7-1 on their surface have been found to trigger a costimulatory signal in T cells (see e.g., Chen, L. et al. (1992) *Cell* 71:1093–1102; Townsend, S. E. and Allison, J. P. (1993) *Science* 259:368–370; and Baskar, S. et al. (1993) *Proc. Natl. Acad. Sci. USA* 90:5687–5690).

In addition to antigen-specific and costimulatory interactions, many other cell surface receptors on T cells are thought to serve an accessory function in T cell activation (reviewed in Clark, E. A. and Ledbetter, J. A. (1994) *Nature* 367:425–428). Examples of such cell surface receptors include: CD4, which interacts with MHC class II antigens; CD8, which interacts with MHC Class I antigens; CD40, which interacts with CD40L (gp39); ICAM-1, which interacts with LFA-1; and CD2 which interacts with LFA-3 (also known as CD58) (Selvaraj, P. et al. (1987) *Nature* 326:400–403). CD2 has been shown to also interact with CD48 and CD59, although with lower affinity than with LFA-3 in humans (Arulanandam, A. R. et al. (1993) *J. Exp. Med.* 177:1439–1450; Sandrin, M. S. et al. (1993) *J. Immunol.* 151:4606–4613).

CD2 is a glycoprotein with a relative molecule mass of 50,000–58,000 which is expressed on thymocytes and mature T cells. CD2 binds to sheep erythrocytes, a property responsible for the phenomenon of T cell E-rosetting. The interaction between CD2 on a T cell and LFA-3 on an APC can facilitate antigen recognition by T cells, thereby stimulating antigen-specific T cell responses (see e.g., Bierer, B. et al. (1988) *J. Exp. Med.* 168:1145; Moingeon, P., et al. (1989) *Nature* 339:312; Koyasu, S. et al. (1990) *Proc. Natl. Acad. Sci. USA* 87:2603; Selvaraj, P. et al. (1987) *Nature* 326:400; and Bierer, B. et al. (1988) *J. Immunol.* 140:3358). This effect has been attributed, at least in part, to increased adhesion between the T cell and the APC, mediated by the CD2/LFA-3 interaction. Additionally, it has been demonstrated that T cells in vitro can be stimulated to proliferate and secrete IL-2 in the absence of APCs using an appropriate combination of anti-CD2 antibodies (see e.g., Meuer, S. et al. (1984) *Cell* 36:897; Feterson, A. et al. (1987) *Nature* 329:842; Yang, Y. S. et al. (1986) *J. Immunol.* 137:1097; and S. C. Meuer, in *Leucocyte Typing IV, White cell differentiation antigens,* W. Knapp et al, Eds (Oxford, 1989) p. 270). For example, T cells can be activated with the anti-CD2 antibody T11.3 in combination with either one of two other anti-CD2 antibodies, T11.2 or T11.1. It has been shown that the T11.3 epitope is a "neo-epitope", which is not exposed on CD2 on resting T cells but is exposed on CD2 upon T cell activation (Meuer, S. et al. (1984) *Cell* 36:897). Although in vitro culture experiments involving CD2 have implicated this surface receptor in T cell-APC adhesion and T cell activation, it is unknown from these studies what physiological role CD2 may serve in T cell responses to antigens.

SUMMARY OF THE INVENTION

The invention pertains to methods for modulating antigen-specific T cell unresponsiveness. The invention encompasses methods for either maintaining or reversing T cell unresponsiveness by inhibiting or stimulating an unresponsive T cell through a cell surface receptor. It has been discovered that antigen-specific T cells which have been rendered unresponsive to an antigen can regain the ability to respond to the antigen by stimulating the T cells through a cell surface receptor, such as CD2. Accordingly, the invention discloses a functional role for CD2 in reversing antigen-specific T cell unresponsiveness (also referred to as T cell anergy).

One embodiment of the invention involves maintaining T cell anergy by contacting anergized T cells with an agent which inhibits stimulation of the T cells through CD2. CD2 inhibitory agents include agents which inhibit an interaction between CD2 and a CD2 ligand (e.g., LFA-3, CD48 or CD59). Such agents include blocking antibodies, soluble forms of CD2 and CD2 ligands, peptides and small molecules. Alternatively, a CD2 inhibitory agent can act intracellularly to inhibit an intracellular signal triggered in the T cell through CD2. Another embodiment of the invention involves reversing T cell anergy by contacting anergized T cells with an agent which stimulates the T cells through CD2. CD2 stimulatory agents include a cell which expresses a CD2 ligand on its surface (e.g., LFA-3, CD48 or CD59), mulivalent forms of a CD2 ligand and stimulatory anti-CD2 antibodies. Alternatively, a CD2 stimulatory agent can act intracellularly to trigger a signal through CD2.

The methods of the invention are useful therapeutically in situations where it is desirable to modulate antigen-specific immune responses, e.g., maintain antigen-specific T cell unresponsiveness or restore antigen-specific T cell responsiveness. For example, it may be necessary to maintain T cell unresponsiveness in a subject who has received an organ or bone marrow transplant to prevent graft rejection by inhibiting stimulation through CD2. In addition, T cell unresponsiveness can be maintained by blocking CD2 stimulation in a subject who has an autoimmune disease to alleviate symptoms of the autoimmune disease. In these cases, a CD2 inhibitory agent is administered to the subject in an amount and over a period of time sufficient to maintain T cell unresponsiveness. Alternatively, T cell unresponsiveness can be reversed in a subject bearing a tumor to stimulate a tumor-specific T cell response or in a subject receiving a vaccine to enhance the efficacy of the vaccine. For example, a cell (e.g., a tumor cell) can be modified to express a CD2 ligand or a CD2 stimulatory agent can be administered to the subject bearing a tumor or who has had a tumor surgically removed to prevent recurrence of th tumor. Additionally, antigen-specific responsiveness can be restored to anergized T cells in vitro by stimulating the T cells through CD2. Responsive T cells generated in vitro can then be administered to a subject.

DETAILED DESCRIPTION OF THE INVENTION

Figure 1:
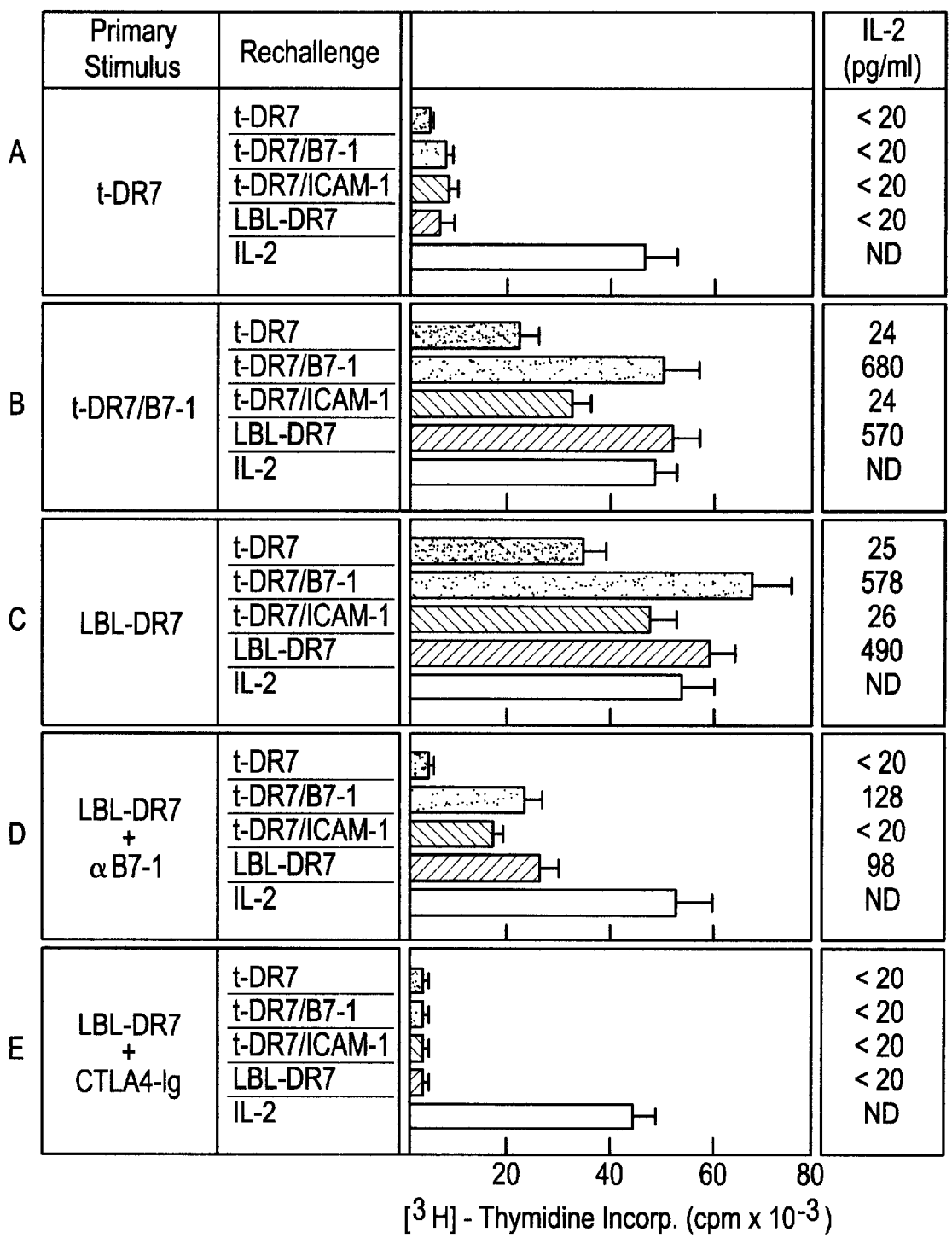
FIG. 1 is a series of bar graphs depicting T cell proliferation and IL-2 production in response to rechallenge by artificial antigen presenting cells or a lymphoblastoid cell line after receiving a primary stimulus.

This invention pertains to methods for modulating antigen-specific T cell unresponsiveness. The term "T cell unresponsiveness" as used herein refers to a reduction in or lack of T cell proliferation, lymphokine secretion or induction of effector functions by a T cell upon exposure to the antigen (or antigenic portion) to which the T cell has been rendered unresponsive. The terms "T cell unresponsiveness" and "T cell anergy" are used interchangeably herein. The methods of this invention provide a means for maintaining or reversing unresponsiveness of a T cell to an antigen in vitro or in vivo. Unresponsive T cells are cells in which T cell unresponsiveness or anergy has been induced by, for example, exposure to an antigen in the absence of a costimulatory signal. Induction of T cell unresponsiveness refers to the initial establishment of a state of T cell anergy. T cell anergy can be induced, for example, by triggering an antigen-specific signal in a T cell (e.g., with an MHC-associated antigenic peptide on an antigen presenting cell) in the absence of a costimulatory signal. Accordingly, the methods of this invention are particularly useful for modulating antigen-specific T cell unresponsiveness in anergic T cells (i.e., T cells in which unresponsiveness or anergy has been previously induced or established). The term "modulation" is intended to include both maintenance of an unresponsive state (i.e., continued T cell anergy) and reversal of an unresponsive state (i.e., restoration of T cell responsiveness).

The methods of the invention involve the use of agents which either inhibit or stimulate an anergized T cell to thereby maintain or reverse T cell anergy. The invention is based, at least in part, on the discovery that a T cell which has been rendered unresponsive to an antigen (for example, by receiving an antigen-specific signal in the absence of a costimulatory signal) can be stimulated to regain the ability to respond to the antigen. Antigen-specific responsiveness of anergized T cells can be restored by stimulating the T cells through a surface receptor, such as CD2, in the presence of the antigen. Accordingly, in one embodiment of the invention, T cell unresponsiveness is maintained by contacting an anergized T cell with an agent which inhibits stimulation of the T cell through CD2. In contrast, methods for reversing T cell unresponsiveness involve contacting an anergized T cell with an agent which stimulates the T cell through CD2. Each of these methods is discussed in detail in the following sub-sections.

I. Methods for Maintaining T Cell Unresponsiveness

One aspect of this invention pertains to methods for maintaining T cell unresponsiveness which are particularly useful in therapeutic situations in which T cell anergy has been induced and it is desirable to preserve the antigen-unresponsive state. Examples of such therapeutic situations include recipients of allogeneic or xenogeneic cell or tissue, such as an organ and bone marrow transplant and subjects having an autoimmune diseases. In these situations, a therapeutic regimen may have induced a state of antigen-specific T cell unresponsiveness in the subject to be treated. For example, antigen-specific T cell unresponsiveness can be induced in a subject by inhibiting a costimulatory signal in T cells, e.g. with an agent CTLA4Ig (see e.g. Turka, L. A. et al. (1992) *Proc. Natl. Acad. Sci. USA* 89:11102–11105; Lenschow, D. J. et al. (1992) *Science* 257:789–792).

In this embodiment of the invention, unresponsiveness of a T cell to an antigen is maintained by contacting the T cell with an agent which inhibits stimulation of the T cell through a CD2 surface receptor. Agents which inhibit stimulation of a T cell through a CD2 surface receptor may result in complete blocking of T cell stimulation through CD2 or may result in partial inhibition of T cell stimulation through CD2, so long as T cell unresponsiveness, as defined herein, is maintained. In one embodiment, the agent which inhibits stimulation of the T cell through a CD2 surface receptor (referred to herein as a CD2 inhibitory agent) acts by blocking an interaction of the CD2 surface receptor with a CD2 ligand. Preferably, the agent blocks an interaction of CD2 with its ligand, LFA-3 (CD58). Alternatively, the agent inhibits an interaction of CD2 with another ligand, such as CD48 or CD59. Agents which can be used to block or inhibit the interaction between CD2 and a CD2 ligand include: antibodies which bind to either CD2 or a CD2 ligand (e.g., blocking antibodies); a soluble form of CD2 (e.g., a truncated form of the molecule which lacks a transmembrane and cytoplasmic domain or a soluble fusion protein, e.g., an immunoglobulin fusion protein) which retains the ability to bind to a CD2 ligand; a soluble form of a CD2 ligand (e.g., a truncated form of the molecule which lacks a transmembrane and cytoplasmic domain or a soluble fusion protein, e.g., an immunoglobulin fusion protein) which retains the ability to bind to CD2); peptides which inhibit the interaction of CD2 and a CD2 ligand; and small molecules which inhibit the interaction of CD2 and a CD2 ligand. Alternatively, a CD2 inhibitory agent can act intracellularly to inhibit an intracellular signal triggered through CD2. Each of these CD2 inhibitory agents is described in detail below.

A. Blocking Antibodies

In one embodiment, a CD2 inhibitory agent is an antibody which binds to either CD2 (i.e., an anti-CD2 antibody) or a CD2 ligand (i.e., an anti-CD2 ligand antibody) to substantially block or inhibit an interaction between CD2 and a CD2 ligand (i.e., blocking antibodies). Anti-CD2 blocking antibodies are described in the art (e.g., TS2/18; see for example Sanchez-Madrid, F. (1982) *Proc. Natl. Acad. Sci. USA* 79:7489) and are commercially available (e.g., anti-Leu 5 from Becton Dickinson, Mountain View, Calif.). Anti-CD2 ligand antibodies include anti-LFA-3 antibodies, anti-CD48 antibodies and anti-CD59 antibodies. Anti-LFA-3 antibodies which can be used to substantially block or inhibit an interaction of CD2 with LFA-3 are known in the art (e.g., TS2/9; see for example Sanchez-Madrid, F. (1982) *Proc. Natl. Acad. Sci. USA* 79:7489). Anti-CD48 blocking antibodies (see e.g., Sandrin, M. S. (1993) *J. Immunol.* 151:4606; and Kato, K. et al. (1993) *Eur. J. Immunol.* 23:1412) and anti-CD59 blocking antibodies (see e.g. Deckert, M. et al. (1992) *Eur. J. Immunol.* 22:2943–2947) are also known in the art.

Additionally, antibodies to CD2 or a CD2 ligand (e.g., LFA-3) can be produced by conventional techniques. Antibodies can be polyclonal, or more preferably, are monoclonal. Polyclonal and monoclonal antibodies can be prepared by standard techniques known in the art. For example, a mammal, (e.g., a mouse, hamster, or rabbit) can be immunized with an antigen (i.e., CD2 or a CD2 ligand), for example with purified protein, recombinant protein, or peptide fragments thereof, or with a cell which expresses the antigen (e.g., expresses CD2 or a CD2 ligand on the cell surface) to elicit an antibody response against the antigen in the mammal. Alternatively, tissue or a whole organ which expresses the antigen can be used to elicit antibodies. The progress of immunization can be monitored by detection of antibody titers in plasma or serum. Standard ELISA or other immunoassay can be used with the antigen to assess the levels of antibodies. Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein ((1975) *Nature* 256:495–497) as well as other techniques such as the human B-cell hybridoma technique (Kozbar et al., (1983) *Immunol. Today* 4:72), and the EBV-hybridoma technique to produce human monoclonal antibodies (Cole et al. (1985) *Monoclonal Antibodies in Cancer Therapy*, Allen R. Bliss, Inc., pages 77–96) can be used. Hybridoma cells can be screened immunochemically for production of antibodies specifically reactive with the antigen and monoclonal antibodies isolated.

Another method of generating specific antibodies, or antibody fragments, reactive against CD2 or a CD2 ligand is to screen expression libraries encoding immunoglobulin genes, or portions thereof, expressed in bacteria with the antigen (or a portion thereof). For example, complete Fab fragments, $V_H$ regions, $F_V$ regions and single chain antibodies can be expressed in bacteria using phage expression libraries. See for example Ward et al., (1989) *Nature* 341:544–546; Huse et al., (1989) *Science* 246:1275–1281; and McCafferty et al. (1990) *Nature* 348:552–554. Alternatively, the SCID-hu mouse can be used to produce antibodies, or fragments thereof.

As used herein, the term "antibody" is intended to include fragments thereof which retain a desired functional property, e.g., the ability to inhibit an interaction between CD2 and a CD2 ligand. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

The term "antibody" is further intended to include derivatives thereof which retain a desired functional property, e.g., the ability to inhibit an interaction between CD2 and a CD2 ligand. Antibody derivatives include chimeric molecules, humanized molecules, molecules with reduced effector functions and bispecific molecules. An antibody, or fragment thereof, produced in a non-human subject can be recognized to varying degrees as foreign when the antibody is administered to a human subject and an immune response against the antibody may be generated in the subject. One approach for minimizing or eliminating this problem is to produce chimeric or humanized antibody derivatives, i.e., antibody molecules comprising portions which are derived from non-human antibodies and portions which are derived from human antibodies. Chimeric antibody molecules can include, for example, the variable region from an antibody of a mouse, rat, or other species, with human constant regions. A variety of approaches for making chimeric antibodies have been described. See, for example, Morrison et al., *Proc. Natl. Acad. Sci. U.S.A.* 81, 6851 (1985); Takeda et al., *Nature* 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. In a further modification, humanized antibodies have only the hypervariable domains of the variable region of non-human origin and have other parts of the variable region of the antibody, especially the conserved framework regions of the antigen-binding domain, of human origin. Such humanized antibodies can be made by any of several techniques known in the art, (e.g., Teng et al., *Proc. Natl. Acad. Sci. U.S.A.,* 80, 7308–7312 (1983); Kozbor et al., *Immunology Today,* 4, 7279 (1983); Olsson et al., *Meth. Enzymol.,* 92, 3–16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain.

For use therapeutically, it is also preferred that an antibody preparation be unable to fix complement or induce other effector functions. Complement fixation can be prevented by deletion of the Fc portion of the antibody, by using an antibody isotype which is not capable of fixing complement, or, less preferably, by using a complement fixing antibody in conjunction with a drug which inhibits complement fixation. Alternatively, amino acid residues within the Fc region which are important for activating complement (see e.g., Tan et al. (1990) *Proc. Natl. Acad. Sci. USA* 87:162–166; Duncan and Winter (1988) *Nature* 332: 738–740) can be mutated to reduce or eliminate the complement-activating ability of an intact antibody. Likewise, amino acids residues within the Fc region which are important for binding of the Fc region to Fc receptors (see e.g., Canfield, S. M. and S. L. Morrison (1991) *J. Exp. Med.* 173:1483–1491; and Lund, J. et al. (1991) *J. Immunol.* 147:2657–2662) can also be mutated to reduce or eliminate Fc receptor binding if an intact antibody is to be used.

An antibody which binds to CD2 or a CD2 ligand can be assessed for blocking or inhibitory activity by conventional techniques. For example, the ability of the antibody to inhibit proliferation and/or lymphokine secretion by activated T cells in an in vitro T cell culture system can be determined (see e.g., Sanchez-Madrid, F. (1982) *Proc. Natl. Acad. Sci. USA* 79:7489). Alternatively, a T cell E-rosetting assay can be used to assess the inhibition of CD2 binding to sheep erythrocytes (a suitable assay is described in Pepinsky, R. B. et al. (1991) *J. Biol. Chem.* 266:18244–18249).

B. Soluble Forms of Receptors and Ligands

Other methods of the invention employ a CD2 inhibitory agent which is a soluble form of CD2 or a CD2 ligand which retains its binding specificity. A soluble form of CD2 or a CD2 ligand can be used to competitively inhibit an interaction between CD2 and a CD2 ligand on the surface of cells. A soluble form of a CD2 ligand such as CD48, CD59, or, preferably, LFA-3 (CD58) can be used to inhibit T cell stimulation through CD2.

In one embodiment, a soluble form of CD2 or a CD2 ligand is a trucated form of the molecule comprising an extracellular domain of the molecule or a functional portion thereof. A portion of the extracellular domain of CD2 which retains the ability to bind to a CD2 ligand can be used. Likewise, a portion of the extracellular domain of a CD2 ligand which retains the ability to bind to CD2 can be used. A soluble truncated form of CD2 or a CD2 ligand can be obtained using standard recombinant DNA techniques, for example by introducing into host cells a recombinant expression vector including a nucleotide sequence encoding the extracellular domain of the molecule, or a functional portion thereof, in a form suitable for expression and secretion of the extracellular domain by the host cells, and isolating the extracellular domain (or portion thereof) from the culture medium.

A recombinant truncated form of CD2 or a CD2 ligand can be designed based upon the nucleotide sequence encoding the protein, by standard techniques. The nucleotide sequence encoding human CD2 is disclosed in Seed, B. and Aruffo, A. (1987) *Proc. Natl. Acad. Sci. USA.* 84:3365–3369. Two forms of the LFA-3 molecule have been described including a typical transmembrane protein. A nucleotide sequence encoding the transmembrane form of LFA-3 is described in Wallner, B. P. et al. (1987) *J. Exp. Med.* 166:923–932. The second form is a glycosyl phosphatidylinositol (GPI)-linked protein. A nucleotide sequence encoding this form of LFA-3 is disclosed in Seed, B. (1987) *Nature* 329:840–842. The GPI-linked form of LFA-3 is anchored to cell membranes by a phospholipid tail. Thus, a soluble form of LFA-3 can be obtained, for example, either by recombinant expression of the extracellular domain of the protein or by cleavage of the phospholipid tail of the GPI-linked form (e.g., using phosphatidylinositol-specific phospholipase C) from the surface of cells expressing this form of LFA-3 to release a soluble form of LFA. Another CD2 ligand, CD48, is a typical transmembrane protein. A nucleotide sequence encoding CD48 is described in Korinek, V. et al. (1991) *Immunogenetics* 33:108–112. Similar to the GPI-linked form of LFA-3, CD59, another CD2 ligand, is a phosphatidylinositol-anchored membrane protein. CD59 can therefor be cleaved from the surface of cells expressing the ligand by phospholipase treatment to obtain a soluble form of CD59. Alternatively, the extracellular domain of CD59 can be expressed recombinantly. A nucleotide sequence encoding human CD59 is disclosed in Sawada, R. et al. (1990) *DNA Cell. Biol.* 9:213–220.

Another soluble form of CD2 or a CD2 ligand for use in the methods of this invention is a fusion protein. The term "fusion protein" as used herein refers to a protein comprised of a first polypeptide from a first protein in contiguous amino acid sequence with a second polypeptide from a second protein. Fusion proteins can be made by standard recombinant DNA techniques wherein a nucleotide sequence encoding the first polypeptide is ligated inframe to a nucleotide sequence encoding the second polypeptide, and these nucleotide sequences are expressed (e.g., using a recombinant expression vector introduced into a host cell) to produce the fusion protein. A preferred fusion protein is an immunoglobulin fusion protein which includes an extracellular domain, or functional portion of CD2 or a CD2 ligand linked to an immunoglobulin heavy chain constant region (e.g., the hinge, CH2 and CH3 regions of a human immunoglobulin such as IgG1). Immunoglobulin fusion proteins can be prepared, for example, according to the teachings of Capon, D. J. et al. (1989) *Nature* 337:525–531 and U.S. Pat. No. 5,116,964 to Capon and Lasky.

Other soluble forms CD2 ligands for use in the methods described herein include a GPI-linked CD2 ligand incorporated into a micelle. CD2 ligands which include a phosphatidylinositol lipid tail to anchor into a membrane (e.g., LFA-3 or CD59) can be isolated as a GPI-linked form and incorporated into a micelle. The LFA-3- or CD59-containing micelles can thus be used to inhibit an interaction between CD2 and a CD2 ligand. LFA-3- or CD59-containing micelles can be prepared as described in WO 89/10938.

In another embodiment of this invention, a soluble form of a CD2 ligand is a multivalent form of the ligand, for example a dimer, trimer or tetramer. Multimers of LFA-3 have been shown to have enhanced activity in blocking an inhibiting LFA-3/CD2 interactions in a T cell E-rosetting assay (see Pepinsky, R. B. et al. (1991) *J. Biol Chem.* 266:18244–18249). Monomers of a CD2 ligand can also be chemically crosslinked to form multimers as described in Pepinsky et al. (cited supra).

C. Peptides and Small Molecules

CD2 inhibitory agents for use in maintaining T cell unresponsiveness further include peptides or small molecules which inhibit or substantially block the interaction of CD2 and a CD2 ligand. For example, a peptide fragment of CD2 or a CD2 ligand which retains the ability to bind to the receptor or ligand and inhibit the interaction of membrane-bound receptor and ligand can be used in the method of the invention. A peptide fragment of CD2 containing an LFA-3 binding domain is disclosed in WO 90/08187. Alternatively, a peptide fragment of LFA-3 containing a CD2 binding domain as disclosed in WO 92/16622 can be used. Other suitable peptides can be prepared and assayed for the ability to inhibit CD2/CD2 ligand interaction, for example by the ability of the peptide to inhibit proliferation and/or lymphokine secretion by activated T cells in an in vitro T cell culture system or by the ability of the peptide to inhibit T cell E-rosetting.

This invention also encompasses the use of small molecules which inhibit an interaction between CD2 and a CD2 ligand to maintain T cell unresponsiveness. For example, a small molecule which mimics the structure of peptide containing an LFA-3 binding region of CD2 or a CD2 binding region of LFA-3 (as discussed above) can be used. Methods for designing such "peptidomimetics" based upon an amino acid sequence of a peptide are known in the art. Alternatively, an in vitro T cell culture system or T cell E-rosetting assay can be used to screen for small molecules which inhibit a CD2/CD2 ligand interaction.

D. Intracellular CD2 Inhibitory Agents

Alternative to an agent which acts extracellularly to inhibit an interaction between CD2 and a CD2 ligand, a CD2 inhibitory agent can act intracellularly to inhibit an intracellular signal triggered in a T cell through the CD2 surface receptor. Intracellular signaling through a CD2 surface receptor on a T cell is mediated through the CD3 complex, and in particular, by the CD3 zeta chain (see Howard, F. D. et al. (1992) *J. Exp. Med.* 176:139–145). Intracellular signals which are induced by this signal transduction pathway include protein tyrosine kinase activity, protein kinase C activity and a rise in intracellular cytosolic free calcium. Accordingly, an agent which inhibits one or more of these intracellular signals induced by T cell stimulation through CD2 can be used as a CD2 inhibitory agent, to maintain T cell unresponsiveness.

Additionally, reversal of T cell anergy by stimulation through CD2 is accompanied by association of the tyrosine kinase JAK-3 with CD2 and by phosphorylation of JAK-3 kinase (see Example 6). Thus, to maintain T cell anergy, JAK-3 activity can be inhibited. Accordingly, a CD2 inhibitory agent can be an agent that inhibits the intracellular activity of a JAK-3 kinase, for example an agent that inhibits the association of JAK-3 kinase with CD2 and/or inhibits the phosphorylation of JAK-3 kinase.

E. Inhibition of Exposure of a T11.3 Neo-epitope

In a method for maintaining T cell unresponsiveness, as described herein, it may also be necessary to inhibit exposure of a T11.3 neo-epitope on the CD2 surface receptor. A "T11.3 neo-epitope" is an epitope on a CD2 molecule which is recognized by (i.e., is bound by) a T11.3 antibody. It has been found that induction of T cell anergy is associated with downmodulation (i.e., reduced or lack of expression) of a T11.3 neo-epitope on CD2 on the anergized T cells. Similarly, reversal of T cell anergy has been found to be associated with re-exposure of the T11.3 neo-epitope on CD2 (see Example 5). For maintenance of T cell unresponsiveness, it may thus be necessary to inhibit exposure of the T11.3 neo-epitope in CD2 on T cells. One agent which has been found to stimulate exposure of the T11.3 neo-epitope on anergized T cells is a T cell growth factor, such as IL-2. Accordingly, to maintain T cell unresponsiveness an agent which inhibits the production or function of a T cell growth factor may be used. A preferred agent for use in maintaining T cell anergy inhibits the production or function of IL-2. Thus, in conjunction with a first agent which inhibits T cell stimulation through CD2, it may be necessary to contact T cells with a second agent which inhibits the function of IL-2, such as an anti-IL-2 antibody or an anti-IL-2 receptor antibody.

F. Uses of CD2 Inhibitory Agents

CD2 inhibitory agents can be administered to a subject for therapeutic purposes, such as to inhibit rejection of an organ or bone marrow transplant, to inhibit graft versus host disease in bone marrow transplantation or to treat an autoimmune disease in a subject. Accordingly, the invention provides a method for maintaining T cell unresponsiveness to an antigen in a subject in which an agent which inhibits T cell stimulation through a CD2 surface receptor is administered to the subject. The term "subject" is intended to include living organisms in which an immune response can be elicited, e.g., mammals. Examples of subjects include humans, monkeys, dogs, cats, mice, rats, and transgenic species thereof.

A CD2 inhibitory agent is administered to subjects in a biologically compatible form suitable for pharmaceutical administration in vivo, in an amount and for a time sufficient to maintain T cell unresponsiveness in the subject. By "biologically compatible form suitable for administration in vivo" is meant a form of the CD2 inhibitory agent to be administered in which toxic effects are outweighed by the therapeutic effects of the agent. Administration of a CD2 inhibitory agent as described herein is in a pharmacological form including a therapeutically active amount of agent alone or in a pharmaceutically acceptable carrier. Administration of a therapeutically active amount of the CD2 inhibitory agent is defined as an amount effective, at dosages and for periods of time necessay to achieve the desired result (e.g., maintain T cell unresponsiveness). For example, a therapeutically active amount of a CD2 inhibitory agent may vary according to factors such as the disease state, age, sex, and weight of the individual, and the ability of agent to elicit a desired response in the individual. Dosage regimens may be adjusted to provide the optimum therapeutic response. For example, several divided doses may be administered daily or the dose may be proportionally reduced as indicated by the exigencies of the therapeutic situation.

The CD2 inhibitory agent may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

To administer a CD2 inhibitory agent by other than parenteral administration, it may be necessary to coat the agent with, or co-administer the agent with, a material to prevent its inactivation. For example, a CD2 inhibitory agent may be administered to an individual in an appropriate carrier or diluent, co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluorophosphate (DEP) and trasylol.

Liposomes include water-in-oil-in-water emulsions as well as conventional liposomes (Strejan et al., (1984) *J. Neuroimmunol* 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be, stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., a CD2 inhibitory agent) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., CD2 inhibitory agent) plus any additional desired ingredient from a previously sterile-filtered solution thereof.

When the active compound is suitably protected, as described above, an agent may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

The timing of administration of a CD2 inhibitory agent can be coordinated with administration of other therapeutic agents to a subject. For example, in a subject wherein T cell unresponsiveness has been induced by administering to the subject an agent which inhibits a T cell costimulatory signal in the subject (e.g., CTLA4Ig), a CD2 inhibitory agent can be administered simultaneously with the agent which inhibits a T cell costimulatory signal or subsequent to administration of the agent which inhibits a T cell costimulatory signal. Additionally, where a CD2 inhibitory agent is maintained at an effective level in vivo, the CD2 inhibitory agent can be administered prior to administration of the agent which inhibits a T cell costimulatory signal. Alternatively, a CD2 inhibitory agent can be administered as an adjunct to other common therapeutic treatments used to inhibit an immune response against an antigen. For example, a CD2 inhibitory agent can be administered as part of a therapeutic regimen that includes administration of an immunosuppressive drug such as cyclosporin A or FK506.

In one embodiment of the invention, T cell unresponsiveness is maintained to an antigen on an allogeneic or xenogeneic cell. Accordingly, the method of the invention can be used to treat a subject who is a recipient of the allogeneic or xenogeneic cell, for example an organ transplant recipient or a bone marrow transplant recipient. The method of the invention is thus useful for inhibiting rejection of transplanted tissues and for inhibiting graft versus host disease in a subject.

In another embodiment of the invention, T cell unresponsiveness is maintained to an autoantigen. Accordingly, the method of the invention can be used to treat a subject suffering from an autoimmune disease or a disorder associated with an inappropriate or abnormal immune response. Examples of autoimmune disease or a disorder associated with an inappropriate or abnormal immune response include rheumatoid arthritis, juvenile rheumatoid arthritis, psoriatic arthritis, psoriasis, leprosy reversal reactions, erythema nodosum leprosum, autoimmune uveitis, multiple sclerosis, allergic encephalomyelitis, systemic lupus erythematosus, acute necrotizing hemorrhagic encephalopathy, idiopathic bilateral progressive sensorineural hearing loss, aplastic anemia, pure red cell anemia, idiopathic thrombocytopenia, polychondritis, scleroderma, Wegener's granulomatosis, chronic active hepatitis, myasthenia gravis, Stevens-Johnson syndrome, idiopathic sprue, lichen planus, Crohn's disease, Graves ophthalmopathy, sarcoidosis, primary biliary cirrhosis, primary juvenile diabetes, dry eye associated with Sjögren's syndrome, uveitis posterior, and interstitial lung fibrosis. The method of the invention is thus useful for alleviating the symptoms of autoimmune diseases and disorder associated with an inappropriate or abnormal immune response.

II. Methods for Inducing and Maintaining T Cell Unresponsiveness

In another embodiment, the invention provides a method for inducing and maintaining T cell unresponsiveness. In this embodiment, a T cell is contacted with a first agent which inhibits T cell stimulation through CD28 or CTLA4 and a second agent which inhibits T cell stimulation through CD2. The first agent is provided to inhibit a costimulatory signal in the T cell, thereby inducing T cell anergy. The second agent is provided to maintain T cell anergy in the unresponsive T cell. Agents which can be used as to inhibit stimulation through CD2 (i.e., a second agent) include the CD2 inhibitory agents described in the previous sections. Agents which can be used to induce T cell unresponsiveness (i.e., a first agent, referred to herein as a CD28/CTLA4 inhibitory agent) include agents which substantially block or inhibit an interaction between CD28 or CTLA4 and a CD28 or CTLA4 ligand. Examples of suitable CD28/CTLA4 inhibitory agents include blocking antibodies which bind to CD28, CTLA4, or a CD28 or CTLA4 ligand (e.g., B7-1 or B7-2); soluble forms of CD28, CTLA4 and CD28 or CTLA4 ligands; and peptides and small molecules which inhibit an interaction between CD28/CTLA4 and a CD28 or CTLA4 ligand. Alternatively, a CD28/CTLA4 inhibitory agent can act intracellularly to inhibit an intracellular signal triggered in the T cell through CD28 or CTLA4.

CD28/CTLA4 inhibitory agents for use in inducing T cell unresponsiveness can be prepared as described above for CD2 inhibitory agents. Blocking antibodies which bind to CD28, B7-1 or B7-2 have been described in the art (see e.g., Damle, N. K., et al. (1981) *Proc. Natl. Acad. Sci. USA* 78:5096–5100; Freedman, A. S. (1987) *J. Immunol.* 137:3260–3267; and Hathcock, K. S. (1993) *Science* 262:905–907) and can be prepared by standard techniques, as described above. Soluble forms of CD28, CTLA4 and B7-1 have also been described in the art (see e.g., Linsley et al. (1991) *J. Exp. Med.* 173:721–730; and Linsley, P. S. et al. (1991) *J. Exp. Med.* 174:561–569) and can be prepared by standard techniques, as described above. Nucleotide sequences for human CD28, CTLA4, B7-1 and B7-2 are available in the art (CD28: Aruffo, A. and Seed, B. (1987) *Proc. Natl. Acad. Sci. USA* 84:8573–8577; CTLA4: Dariavach, P. et al. (1988) *Eur. J. Immunol.* 18:1901–1905; B7-1: Freeman, G. J. et al. (1989) *J. Immunol.* 143:2714–2722; B7-2: Freeman, G. J. et al. (1993) *Science* 262:909–911 and Azuma, M. et al. (1993) *Nature* 366:76–79). A preferred CD28/CTLA4 inhibitory agent is a CTLA4Ig fusion protein, as described in Linsley, P. S. et al. (1991) *J. Exp. Med.* 174:561–569.

To induce and maintain T cell unresponsiveness, a T cell can be contacted with a CD28/CTLA4 inhibitory agent and a CD2 inhibitory agent, simultaneously, or sequentially. When contacted sequentially, it is preferred that the T cell be contacted first with the CD28/CTLA4 inhibitory agent and then with the CD2 inhibitory agent.

This method is also useful therapeutically, in situations where it is desirable to inhibit an antigen-specific immune response, for example in organ transplantation, bone marrow transplantation and autoimmune diseases. For therapeutic purposes, a CD28/CTLA4 inhibitory atent and a CD2 inhibitory agent are administered to a subject to induce and maintain T cell unresponsiveness. These agents can be administered to a subject simulateneously or sequentially. Routes of administration, pharmaceutical compositions for administration, timing and dosages of administration and other considerations for administration are as described above for CD2 inhibitory agents.

III. Methods for Restoring T Cell Responsiveness

The invention further provides methods for restoring responsiveness of an anergized T cell to an antigen (i.e., reversing anergy). These methods restore the ability of an anergized T cell to respond (e.g., proliferate and secrete IL-2) upon subsequent stimulation of the T cell by an antigen and a costimulatory molecule. This method is useful in therapeutic situations where it is desirable to stimulate an immune response against an antigen by anergized T cells. An example of this situation is a tumor-bearing subject in whom the presence of the tumor has rendered T cells unresponsive to tumor antigens.

In one embodiment, T cell responsiveness to an antigen is restored by contacting an anergized T cell in the presence of the antigen with an agent which stimulates the T cell through a CD2 surface receptor. The method provides a means by which T cell responsiveness is fully, or partially restored (as compared to the responsiveness of the T cell prior to being anergized) such that the T cell responds (i.e., proliferates, secretes Il-2) to subsequent stimulation by the antigen and a costimulatory molecule. An agent which stimulates the T cell through a CD2 surface receptor is refered to herein as a CD2 stimulatory agent. To restore T cell responsiveness, a CD2 stimulatory agent can be a cell which expresses a CD2 ligand on its surface. Alternatively, a CD2 stimulatory agent can be a soluble, stimulatory form of a CD2 ligand (e.g., a multivalent form or a micellar form). In addition, the CD2 stimulatory agent can be at least one anti-CD2 antibody or a combination thereof. A CD2 stimulatory agent useful in the methods of this invention can also be an agent which acts intracellularly to stimulate an intracellular signal triggered by CD2.

A. Cells Expressing a CD2 Ligand

In one embodiment in a method to restore T cell responsiveness to an antigen, a CD2 stimulatory agent is a cell expressing a CD2 ligand on its surface. Preferably, the CD2 ligand is LFA-3 (CD58). Alternatively, a CD2 ligand can be CD48 or CD59. Thus, to restore T cell responsiveness to an antigen, an unresponsive T cell can be contacted with a cell which expresses a CD2 ligand (e.g., LFA-3) and the antigen on its surface. A cell which does not naturally express a CD2 ligand can be modified to express a CD2 ligand. For example, a tumor cell, which constitutively expresses tumor antigens but fails to express LFA-3, can be modified to express LFA-3. A tumor cell can also be modified to express CD48 or CD59. Alternatively, a cell may express a CD2 ligand(s) on its cell surface but in amount insufficient to reverse T cell anergy. In such a case, the level of expression of a CD2 ligand can be increased on a cell surface. A cell is "modified to express a CD2 ligand" in a manner which results in expression of a CD2 ligand on the cell surface. Prior to modification, the cell may be incapable of expressing a CD2 ligand, may be capable of expressing a CD2 ligand but fail to do so, or may express insufficient amounts of a CD2 ligand. Therefore, a cell can be modified to express a CD2 ligand by any one of a number of techniques e.g., by introducing nucleic acid encoding the CD ligand into the cell, coupling a CD2 ligand to the cell surface or stimulating expression of a CD2 ligand on the cell surface.

A preferred method for modifying a cell to express a CD2 ligand is to introduce into the cell a nucleic acid which encodes the CD2 ligand, such as LFA-3, in a form suitable for expression of the CD2 ligand on the cell surface. A nucleic acid encoding a CD2 ligand (e.g., a recombinant expression vector) can be introduced into a host cell by one of a variety of techniques useful for introduction of nucleic acids into mammalian cells (generally termed transfection), including electroporation, calcium-phosphate precipitation, DEAE-dextran treatment, lipofection, microinjection and infection with viral vectors. Suitable methods for transfecting mammalian cells can be found in Sambrook et al. (*Molecular Cloning: A Laboratory Manual, 2nd Edition.* Cold Spring Harbor Laboratory press (1989)) and other laboratory textbooks. The nucleic acid to be introduced can be, for example, DNA including the gene encoding the CD2 ligand, sense strand RNA encoding the CD2 ligand or a recombinant expression vector containing a cDNA encoding the CD2 ligand. Preferred cDNAs to use are those for the transmembrane form of human LFA-3 (disclosed in Wallner, B. P. et al. (1987) *J. Exp. Med.* 166:923–932) and the GPI-linked form of human LFA-3 (disclosed in Seed, B. (1987) *Nature* 329:840–842). Alternatively, cDNAs for human CD48 (disclosed in Korinek, V. et al. (1991) *Immunogenetics* 33:108–112) and human CD59 (disclosed in Sawada, R. et al. (1990) *DNA Cell. Biol.* 9:213–220) can be used. Additionally, a cell can be modified to express multiple CD2 ligands. Various combinations of LFA-3 (both forms), CD48 and CD59 which can be expressed on cells will be apparent to those skilled in the art., The nucleic acid encoding a CD2 ligand which is introduced into a cell is in a form suitable for expression of the CD2 ligand on the cell surface. The nucleic acid contains the necessary coding and regulatory sequences required for transcription and translation of a gene, which may include promoters, enhancers and polyadenylation signals, and sequences necessary for transport of the molecule to the surface of the tumor cell, including N-terminal signal sequences. When the nucleic acid is a cDNA in a recombinant expression vector, the regulatory functions responsible for transcription and/or translation of the cDNA are often provided by viral sequences. Examples of commonly used viral promoters include those derived from polyoma, Adenovirus 2, cytomegalovirus and Simian Virus 40, and retroviral LTRs. Regulatory sequences linked to the cDNA can be selected to provide constitutive or inducible transcription, by, for example, use of an inducible promoter, such as the metallothionein promoter or a glucocorticoid-responsive promoter.

A preferred approach for introducing nucleic acid encoding a CD2 ligand into cells (e.g., tumor cells) is by use of a viral vector containing nucleic acid, e.g. a cDNA, encoding the CD2 ligand. Examples of viral vectors which can be used include retroviral vectors (Eglitis, M. A., et al. (1985) *Science* 23:1395–1398; Danos, O. and Mulligan, R. (1988) *Proc. Natl. Acad Sci. USA* 85:6460–6464; Markowitz, D., et al. (1988) *J. Virol.* 62:1120–1124), adenoviral vectors (Rosenfeld, M. A., et al. (1992) *Cell* 68:143–155) and adeno-associated viral vectors (Tratschin, J. D., et al. (1985) *Mol. Cell. Biol.* 5:3251–3260). Infection of tumor cells with a viral vector has the advantage that a large proportion of cells will receive nucleic acid, thereby obviating a need for selection of cells which have received nucleic acid, and molecules encoded within the viral vector, e.g. by a cDNA contained in the viral vector, are expressed efficiently in cells which have taken up viral vector nucleic acid.

Alternatively, a CD2 ligand can be expressed on a cell using a plasmid expression vector which contains nucleic acid, e.g., a cDNA, encoding the CD2 ligand. Suitable plasmid expression vectors include CDM8 (Seed, B., *Nature* 329, 840 (1987)) and pMT2PC (Kaufinan, et al., *EMBO J.* 6, 187–195 (1987)). Since only a small fraction of cells (about 1 out of $10^5$) typically integrate transfected plasmid DNA into their genomes, it is advantageous to transfect a nucleic acid encoding a selectable marker into the cell along with the nucleic acid(s) of interest to allow for selection of transfected cells. Preferred selectable markers include those which confer resistance to drugs such as G418, hygromycin and methotrexate. Selectable markers may be introduced on the same plasmid as the gene(s) of interest or may be introduced on a separate plasmid. Following selection of transfected cells using the appropriate selectable marker(s), expression of the costimulatory molecule on the surface of the cell can be confirmed by immunofluorescent staining of the cells. For example, cells may be stained with a fluorescently labeled monoclonal antibody reactive against the CD2 ligand or with a fluorescently labeled soluble receptor which binds the CD2 ligand (e.g. soluble CD2). Antibodies which can be used to detect LFA-3 are disclosed in Sanchez-Madrid, F. (1982) *Proc. Natl. Acad. Sci. USA* 79:7489 (e.g., TS2/9); antibodies which can be used to detect CD48 antibodies are disclosed in Sandrin, M. S. (1993) *J. Immunol.* 151:4606 and Kato, K. et al. (1993) *Eur. J. Immunol.* 23:1412; antibodies which can be used to detect CD59 are disclosed in Deckert, M. et al. (1992) *Eur. J. Immunol.* 22:2943–2947.

When transfection of cells (e.g., tumor cells) leads to modification of a large proportion of the cells and efficient expression of a CD2 ligand on the surface of the cells, e.g., when using a viral expression vector, cells may be used without further isolation or subcloning. Alternatively, a homogenous population of transfected cells can be prepared by isolating a single transfected cell by limiting dilution cloning followed by expansion of the single cell into a clonal population of cells by standard techniques.

Alternative to introducing a nucleic acid encoding a CD2 ligand into a cell, a cell can be modified to express a CD2 ligand by inducing or increasing the level of expression of the CD2 ligand on the cell surface. An agent which stimulates expression of a CD2 ligand can be used in order to induce or increase expression of a CD2 ligand on a cell surface. For example, cells can be contacted with the agent in vitro in a culture medium. The agent which stimulates expression of a CD2 ligand may act, for instance, by increasing transcription of a CD2 ligand gene, by increasing translation of a CD2 ligand mRNA or by increasing stability or transport of a CD2 ligand to the cell surface. Another agent which can be used to induce or increase expression of a CD2 ligand on a tumor cell surface is a nucleic acid encoding a transcription factor which upregulates transcription of the gene encoding the CD2 ligand. This nucleic acid can be transfected into the cell, as described previously, to cause increased transcription of the CD2 ligand gene, resulting in increased cell-surface levels of the CD2 ligand.

Alternatively, a cell (e.g., tumor cell) can be modified to express a CD2 ligand by coupling a CD2 ligand to the surface of the cell. For example, a CD2 ligand can be obtained using standard recombinant DNA technology and expression systems which allows for production and isolation of the CD2 ligand protein. Alternatively, a CD2 ligand can be isolated from cells which express the CD2 ligand using standard protein purification techniques. The isolated CD2 ligand is then coupled to the cell surface. The terms "coupled" or "coupling" refer to a chemical, enzymatic or other means by which a CD2 ligand is linked to a cell such that the CD2 ligand is present on the surface of the cell and is capable of triggering a signal in T cells through CD2. For example, the CD2 ligand can be chemically crosslinked to the cell surface using commercially available crosslinking reagents (e.g. from Pierce, Rockford Ill.). Another approach is to couple a GPI-linked form of a CD2 ligand, such as LFA-3 or CD59, to a cell surface through insertion of the lipid tail of the molecule into the cell membrane. Still yet another approach involves coupling a CD2 ligand to a cell through a bispecific antibody which binds both the CD2 ligand and a cell-surface molecule on the cell. Fragments, mutants or variants of CD2 ligands which retain the ability to trigger a signal in T cells via CD2 when coupled to the surface of a cell can also be used.

B. Soluble, Stimulatory Forms of CD2 Ligands

In other embodiments of the invention, the CD2 stimulatory agent used to restore T cell responsiveness is a soluble, stimulatory form of a CD2 ligand. Soluble forms of CD2 ligands have been shown to trigger a signal through CD2 in combination with an appropriate anti-CD2 antibody. In one embodiment, the soluble, stimulatory form of a CD2 ligand is a multivalent form of a CD2 ligand, for example a dimer, trimer or tetramer. Multimers of LFA-3 have been shown to trigger T cell activation in vitro in combination with an appropriate anti-CD2 antibody (e.g., a T11.3 antibody) (see Pepinsky, R. B. et al. (1991) *J. Biol Chem.* 266:18244–18249). Accordingly, multimers of a CD2 ligand which stimulate T cell activation through CD2 can be used as CD2 stimulatory agents. Preferably, a multivalent form of a CD2 ligand is used in combination with an anti-CD2 antibody which binds to the T11.3 epitope (e.g., with the T11.3 antibody). Monomers of a CD2 ligand can be chemically crosslinked to form multimers as described in Pepinsky et al. (cited supra).

In yet another embodiment, the soluble, stimulatory form of a CD2 ligand is a GPI-linked CD2 ligand incorporated into a micelle. CD2 ligands which include a phosphatidylinositol lipid tail to anchor into a membrane (e.g., LFA-3 or CD59) can be isolated as a GPI-linked form and incorporated into a micelle. LFA-3- or CD59-containing micelles can be prepared as described in WO 89/10938. A micellar form of a CD2 ligand in combination with an appropriate anti-CD2 antibody, e.g. a T11.3 antibody, can also be used to stimulate a T cell through CD2 (see WO 89/10938).

C. Stimulatory Anti-CD2 Antibodies

In another aspect of this invention, the agent which stimulates the T cell through a CD2 surface receptor is at least one anti-CD2 antibody. Stimulatory forms of anti-CD2 antibodies are described in the art. Preferably, stimulation through CD2 with anti-CD2 antibodies is accomplished using a combination of at least two different anti-CD2 antibodies. Stimulatory combinations of anti-CD2 antibodies which have been described include the following: the T11.3 antibody in combination with the T11.1 or T11.2 antibody (Meuer, S. C. et al. (1984) *Cell* 36:897–906) and the 9.6 antibody (which recognizes the same epitope as T11.1) in combination with the 9-1 antibody (Yang, S. Y. et al. (1986) *J. Immunol.* 137:1097–1100). Other antibodies which bind to the same epitopes as these antibodies can also be used. Additional stimulatory anti-CD2 antibodies, or combinations of antibodies, can be prepared and identified by standard techniques. For example, a stimulatory antibody or combination of antibodies can be identified based upon the ability of the antibody or antibodies to stimulate T cell proliferation in the absence of antigen presenting cells in an in vitro T cell culture system.

D. Intracellular CD2 Stimulatory Agents

Alternative to an agent which acts extracellularly to stimulate a T cell through CD2, a CD2 stimulatory agent can act intracellularly to stimulate an intracellular signal triggered in a T cell through the CD2 surface receptor. As discussed above, intracellularly signaling through a CD2 surface receptor on a T cell is mediated through the CD3 complex and induces protein tyrosine kinase activity, protein kinase C activity and a rise in intracellular cytosolic free calcium. Accordingly, an agent which stimulates one or more of these intracellular signals induced by T cell stimulation through CD2 can be used as a CD2 stimulatory agent to restore T cell responsiveness.

Additionally, as discussed above, reversal of T cell anergy is accompanied by association of the tyrosine kinase JAK-3 with CD2 and by phosphorylation of JAK-3 kinase (see Example 6). Accordingly, an intracellular CD2 stimulatory agent can be an agent that stimulates the intracellular activity of JAK-3 kinase, for example an agent that stimulates the association of JAK-3 kinase with CD2 and/or stimulates the phosphorylation of JAK-3 kinase.

E. Priming of an Unresponsive T Cell

In addition to contacting an anergized T cell with a CD2 stimulatory agent, it may be necessary to "prime" a T cell for stimulation through CD2 to restore antigen-specific responsiveness in the T cell. The term "prime" a T cell is used herein to describe a treatment of a T cell which prepares the T cell for subsequent stimulation, e.g., through CD2. Accordingly, an anergized T cell can be first contacted with an agent which primes the T cell for stimulation through a CD2 surface receptor. In one embodiment, an agent which primes a T cell for stimulation through CD2 is a T cell growth factor, preferably IL-2. Other T cell growth factors which can be used to prime an anergized T cell include IL-4 and IL-7. The receptors for each of these three lymphokines (IL-2, IL-4 and IL-7) utilize a common signaling subunit, the IL-2 gamma chain, and thus trigger similar intracellular signals. Other cytokines which bind to a receptor utilizing an IL-2 receptor gamma chain for intracellular signaling or agents which function intracellularly to trigger the IL-2 receptor gamma chain signaling pathway can be used to prime T cells.

Alternatively, an agent which primes an unresponsive T cell stimulates exposure of a T11.3 neo-epitope on the CD2 surface receptor on the T cell. Accordingly, exposure of a T11.3 epitope on CD2 can be used as one assessment of T cell priming. Exposure of the T11.3 epitope on CD2 on T cells can be assessed by the determining the ability of the T11.3 antibody to bind to the T cells (e.g., by flow cytometry). A preferred agent that can be used to expose a T11.3 neo-epitope on CD2 is IL-2.

According to this aspect of the invention, an unresponsive T cell can be contacted with an agent which primes the T cell prior to contact with a CD2 stimulatory agent. For example, a T cell can be cultured in IL-2 to prime the T cell for stimulation through CD2 prior to being stimulated with a cell expressing a CD2 ligand or with stimulatory anti-CD2 antibodies.

F. Uses of CD2 Stimulatory Agents

The methods of the invention for restoring responsiveness of T cells to an antigen can be used for therapeutic purposes. For example, the antigen can be an antigen expressed on tumor cells and the method can be used to enhance anti-tumor responsiveness. Alternatively, the method can be used to enhance responsiveness to pathogenic agents, such as viruses, bacteria, parasites and fungi or to enhance the efficacy of vaccines against such pathogenic agents. For example, a CD2 stimulatory agent can be administered to a subject infected with a pathogenic agent or can be coadministered with a vaccine to enhance the responsiveness of T cells to antigens of the vaccine. The method can also be used as an adjunct to therapeutic treatments which include in vitro T cell culture, since T cells are prone to becoming antigen unresponsive upon culture in vitro. Accordingly, the method of the invention can be used to increase the antigen responsiveness of in vitro cultured T cells which are to be used therapeutically.

Antigen-specific responsiveness of an anergized T cell can be restored by contacting an anergized T cell with a CD2 stimulatory agent either in vivo or ex vivo. An antigen-specific T cell is contacted with the CD2 stimulatory agent preferably in the presence of the antigen. For example, the T cell is contacted with the CD2 stimulatory agent in culture in vitro in the presence of cells expressing the antigen or in vivo wherein the antigen is present endogenously or the antigen is coadministered with the CD2 stimulatory agent. A T cell can further be contacted with an agent which primes the T cell for stimulation through CD2 either in vitro or in vivo. For example, T cells can be incubated in vitro with IL-2 or IL-2 can be administered systemically to a subject.

Routes of administration, pharmaceutical compositions for administration, timing and dosages of administration and other considerations for administration of CD2 stimulatory agents are as described above for CD2 inhibitory agents, or easily adapted therefrom. In addition to compositions previously described for CD2 inhibitory agents, CD2 stimulatory agents can further be administered with an adjuvant. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. When a CD2 stimulatory agent is co-administered with another therapeutic agent, for example with a vaccine, the timing and dosage of the CD2 stimulatory agent can be coordinated with the timing and dosage of administration of the other agent for maximal efficacy of both therapeutic agents.

IV. Methods for Restoring a T Cell Response to an Antigen

An antigen-specific, anergized T cell which is stimulated through CD2 according to a method of the invention regains the ability to respond to the antigen upon exposure to the antigen together with a stimulus which triggers a costimulatory signal. Accordingly, the invention further provides a method for restoring a response to an antigen by a T cell which is unresponsive to the antigen in which the T cell is contacted, in the presence of the antigen, with a first agent which stimulates the T cell through a CD2 surface receptor. In addition, the T cell is contacted with a second agent which stimulates the T cell through a CD28 or CTLA4 surface receptor. The method can be used therapeutically to enhance an anti-tumor response in a tumor-bearing subject. Alternatively, the method for restoring a response to an antigen can be used for such therapeutic purposes, as stimulating an immune response against a pathogenic agent (e.g., bacteria, virus, parasite or fungus) and stimulating the efficacy of vaccination against a pathogenic agent.

Examples of first agents to be used in this method are the CD2 stimulatory agents described in detail above. Examples of second agents for use in the method include a cell which expresses a CD28 or CTLA4 ligand (e.g., a cell which has been modified to express a CD28 or CTLA4 ligand as described previously for CD2 ligands), a stimulatory form of a CD28 or CTLA4 ligand (e.g., a multivalent form) or stimulatory antibodies which bind to CD28 or CTLA4 (e.g., a stimulatory anti-CD28 antibody as described in Harding, F. A. (1992) *Nature* 356:607–609). Preferred CD28 and CTLA4 ligands are B7-1 and B7-2.

In a preferred embodiment, the first agent is a CD2 ligand on the surface of a cell and the second agent is a CD28 or CTLA4 ligand on the surface of the same or another cell. A preferred CD2 ligand is LFA-3. Alternatively, the CD2 ligand can be CD48 or CD59. Preferred CD28 and CTLA4 ligands are B7-1 and B7-2. A cell can be modified to express a CD2 ligand and/or a CD28/CTLA4 ligand by a method described previously. For example, a nucleic acid encoding the CD2 ligand and/or CD28/CTLA4 ligand can be introduced into the cell in a form suitable for expression of the ligand(s) on the cell surface. Alternatively, CD2 and/or CD28/CTLA4 ligands can be induced on cells or coupled to the surface of cells.

To restore T cell responsiveness to an antigen, it may be necessary to contact T cells with a third agent which primes the T cells for stimulation through CD2. Agents for priming a T cell are described above. A preferred agent for priming T cells and for stimulating exposure of a T11.3 neo-epitope on CD2 on T cells is IL-2. The T cells can be contacted with the agent which primes the T cells for stimulation through CD2 prior to being contacted with the an agent which stimulates the T cell through CD2. A T cell can be contacted with an agent which primes the T cell for stimulation through CD2 either in vitro or in vivo. For example, T cells can be obtained from a subject and cultured in vitro in IL-2 prior to being readministered to the subject or IL-2 can be administered systemically to a subject.

In a preferred embodiment, the invention provides a method for restoring a tumor specific T cell response in a tumor-bearing subject comprising modifying tumor cells to express a CD2 ligand and a CD28 or CTLA4 ligand. Preferably, tumor cells are modified to express a CD2 ligand and a CD28 or CTLA4 ligand by introducing into the tumor cells at least one nucleic acid encoding the CD2 ligand and the CD28 or CTLA4 ligand in a form suitable for expression of the CD2 ligand and the CD28 or CTLA4 ligand on the tumor cells' surface. Tumor cells can be modified in vivo or ex vivo. For example, a tumor cell can be modified to express a CD2 ligand in vivo by infection of tumor cells with a recombinant virus which encodes the CD2 ligand in a form suitable for expression of the CD2 ligand on the surface of the tumor cell. Alternatively, tumor cells can be removed from a subject, modified ex vivo to express a CD2 ligand and readministered to the subject. When modified ex vivo, a sample of tumor cells can be modified to express both ligands (i.e., a CD2 ligand and a CD28 or CTLA4 ligand), or alternatively, one sample of tumor cells can be modified to express a CD2 ligand and a second sample of tumor cells can be modified to express a CD28 or CTLA4 ligand. The two samples of tumor cells can then be administered to a subject simultaneously or sequentially. It may be beneficial to first administer a sample of tumor cells which express a CD2 ligand to restore tumor-specific responsiveness, followed by administration of a sample of tumor cells which express a CD28 or CTLA4 ligand to stimulate an tumor-specific T cell response.

Tumor-specific T cells can also be stimulated either in vivo or ex vivo. For example, T cells can be stimulated in vivo by modifying tumor cells in vivo or by administering modified tumor cells (or other CD2 stimulatory agents) to the subject. Alternatively, T cells can be obtained from a subject, stimulated ex vivo (e.g., with an LFA-3-bearing tumor cell or with a tumor cell and anti-CD2 antibodies) and then readministered to the subject. T cells stimulated in vitro can first be cultured in vitro with IL-2 to prime the T cells or IL-2 can be administered systemically to the subject to prime T cells for stimulation through CD2.

Accordingly, this invention also provides tumor cells modified to express a CD2 ligand, wherein the tumor cells do not express the CD2 ligand prior to modification. Preferably, the tumor cells are modified to express LFA-3. The invention also provides a tumor cell which is modified to express a CD2 ligand and a CD28 or CTLA4 ligand, wherein the tumor cell does not express the CD2 ligand and the CD28 or CTLA4 ligand prior to modification. Tumor cells modified to express LFA-3 and B7-1 or B7-2 are preferred. Tumor cells can be modified to express a CD2 ligand and optionally a CD28 or CTLA4 ligand as previously described. Modified tumor cells can be incorporated into a composition suitable for pharmaceutical administration. For example, tumor cells can be administered in a pharmaceutically acceptable carrier or diluent (e.g., a sterile saline solution). Tumor cells can be administered by an appopriate route which delivers the tumor cells to a desired location, e.g., by intravenous, subcutaneous, intramuscular or intraperitoneal injection.

This invention is further illustrated by the following examples which should not be construed as limiting. The contents of all references and published patents and patent applications cited throughout the application are hereby incorporated by reference.

EXAMPLE 1
Induction of T Cell Unresponsiveness by Inhibition of a Costimulatory Signal in the T Cell In the examples, two helper T cell clones (TC-1, TC-2) specific for the alloantigen HLA-DR7 were used. These clones are $CD4^+$ $CD8^-$ $CD28^+$ and were generated using standard methodology (as described in J. Goronzy, et al. (1987) *Methods Enzymol.* 150:333). In some experiments, the T cell clones were stimulated with NIH-3T3 or COS cells transfected to express HLA-DR7 and or other cell surface molecules. These transfected cells are referred to herein as artificial alloantigen presenting cells (allo-APCs). Prior to transfection, these cells are unable to stimulate T cell proliferation or IL-2 production. The transfectants are designated by the molecules they express on their surface as follows: Cells expressing HLA-DR7 alone are designated t-DR7, cells expressing both HLA-DR7 and B7-1 are designated t-DR7/B7-1, cells expressing HLA-DR7 and ICAM-1 are designated t-DR7/ICAM-1 etc. In other experiments, the T cell clones were stimulated with a HLA-DR7 homozygous lymphoblastoid cell line which co-expresses HLA-DR7, B7-1 (CD80), B7-2, ICAM-1 (CD54), and LFA-3 (CD58). This cell line is designated LBL-DR7. T cell responses were assayed by measuring T cell proliferation or IL-2 production by standard techniques. The results with both clones were consistently comparable. Only results with TC-1 are presented.

In a first series of experiments, TC-1 was co-cultured for 72 hrs with either t-DR7, t-DR7/B7-1 or LBL-DR7. TC-1 and allo-APCs or LBL-DR7 were cultured ($2.5 \times 10^4$ cells/well) at the optimal 1:1 ratio. After 72 hrs of primary culture, TC-1 cells were isolated from artificial allo-APCs by Percoll gradient centrifugation and from LBL-DR7 by Ficoll separation, washed extensively and cultured in medium without IL-2 for 24 hrs. Each population was subsequently rechallenged with a secondary stimulus, either artificial allo-APCs (t-DR7, t-DR7/B7, t-DR7/ICAM-1), LBL-DR7 cells, or IL-2. Artificial allo-APCs and LBL-DR7 cells were treated with 20 µg/ml mitomycin-C (Sigma Chemical Co., St. Louis, Mo.) at 37° C. for 2 h, and washed extensively. LBL-DR7 cells were irradiated at 9600 rads for some experiments. Anti-B7-1 (133) mAb and CTLA4-Ig fusion protein were added to certain cultures (indicated in FIG. 1) at 10 µg/ml. Recombinant human IL-2 (Collaborative Biomedical Products, Bedford, Mass.) was used at 100 IU/ml. Proliferation was measured by [$^3$H] thymidine (1 µCi) (DuPont, Boston, Mass.) incorporation for the last 16 hrs of a 72-hr incubation. IL-2 accumulation was measured by enzyme-linked immunosorbent assay (Biosource, Camarillo, Calif.) in supernatants harvested 24 hrs after the initiation of culture. Results are representative of 7 experiments. The results are shown in FIG. 1, wherein black bars represent response of TC-1 cells to artificial allo-APCs, hatched bars represent response to LBL-DR7 and clear bars represent response to exogenous recombinant human IL-2.

Primary culture of TC-1 with t-DR7 induced T cell unresponsiveness (i.e., anergy), as evidenced by the lack of a response on rechallenge of TC-1 with allo-APCs or LBL-DR7 (see FIG. 1, panel A). This experiment confirms that stimulation of an antigen-specific signal in TC-1 in the absence of a costimulatory signal (e.g., in the absence of binding to B7-1) induces T cell unresponsiveness. In contrast, primary culture with either t-DR7/B7-1 or LBL-DR7 resulted in a significant secondary proliferative response and IL-2 accumulation (see FIG. 1, panels B, C). Addition of an anti-B7-1 mAb (described in A. S. Freedman, et al. (1987) *J. Immunol.* 137:3260), to LBL-DR7 cells in the primary culture resulted in reduced proliferation and IL-2 accumulation but did not induce unresponsiveness on rechallenge (see FIG. 1, panel D). This is due to the inability of the anti-B7-1 antibody to inhibit an interaction between other B7 family members (e.g., B7-2) and their receptors on T cells (e.g., CD28 and/or CTLA4). However, primary culture with LBL-DR7 in the presence of CTLA4-Ig (described in C. D. Gimmi, et al. (1993) *Proc. Natl. Acad. Sci. USA* 90:6586), resulted in anergy (see FIG. 1, panel E). This is due to the ability of CTLA4Ig to inhibit the interaction of all B7 family members with their receptors on T cells. In all instances, anergized and non-anergized cells responded equally well to exogenous IL-2. These results demonstrate that blockade of the B7 family of costimulatory molecules is necessary and sufficient to induce alloantigen-specific anergy, since all other surface molecules expressed on LBL-DR7 cells that are not blocked by CTLA4-Ig could not prevent the induction of anergy in the presence of CTLA4Ig. Moreover, following the induction of anergy, neither B7 family members nor other non-B7 costimulatory molecules expressed on LBL-DR7 cells appear to be capable of reversing this state.

Figure 2:
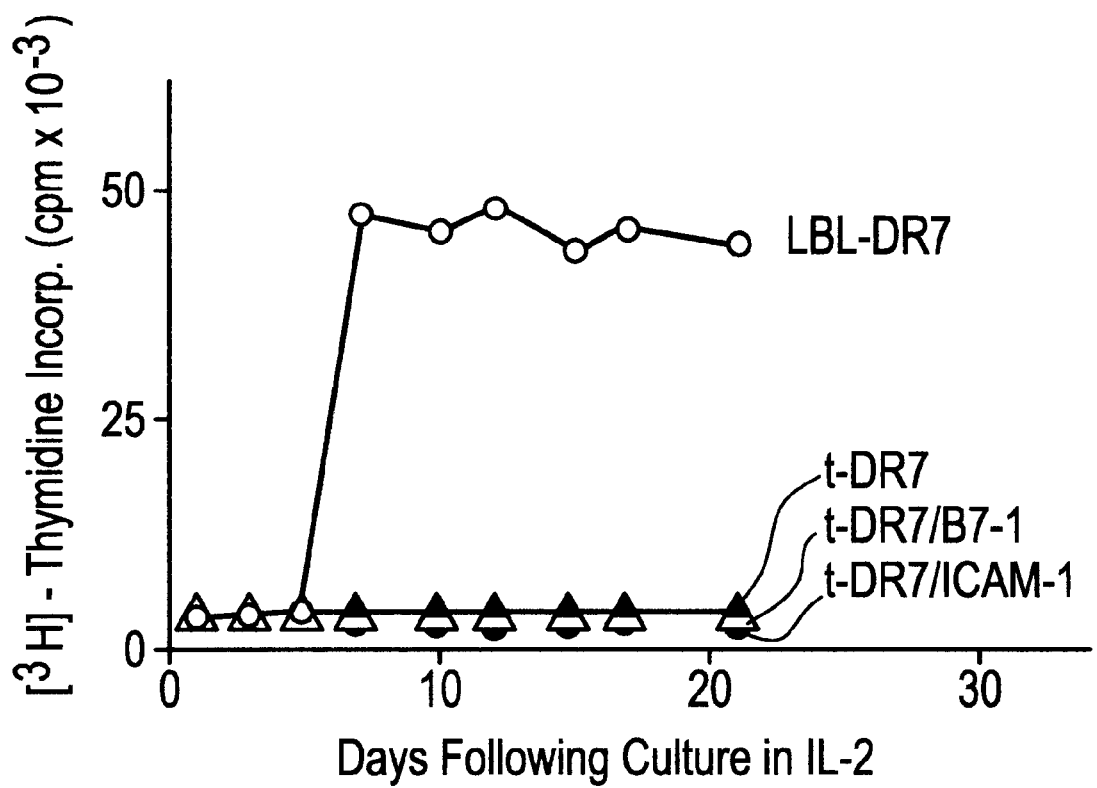
FIG. 2 is a graph depicting proliferation of anergized T cells following culture in IL-2 and stimulation by artificial antigen presenting cells or a lymphoblastoid cell line.

EXAMPLE 2
Stimulation of T Cells with B7-1 or ICAM-1 Does Not Reverse T Cell Unresponsiveness In a second series of experiments, anergized TC-1 cells were cultured in IL-2 for 3 to 21 days to determine whether IL-2 could restore responsiveness to specific alloantigen. TC-1 cells were first anergized by primary co-culture with t-DR7 (as described in Example 1) and then incubated in IL-2 for 3 to 21 days. These TC-1 cells were rechallenged with allo-APCs or LBL-DR7 (at the time intervals indicated in FIG. 2) following IL-2 incubation. Results shown in FIG. 2 are representative of five experiments. At any time point up to 21 days following IL-2 incubation, rechallenge with t-DR7, t-DR7/B7-1, or t-DR7/ICAM-1 did not restore responsiveness (see FIG. 2) at a wide range of stimulator-:responder ratios. In contrast, after at least 7 days of IL-2 culture, rechallenge with LBL-DR7, induced a proliferative response (see FIG. 2) which was associated with significant accumulation of IL-2. These experiments indicate that following prolonged IL-2 culture, alloantigen-specific responsiveness of TC-1 can be restored by culture with LBL-DR7, but neither B7-1 nor ICAM-1 (on allo-APCs) appear to be sufficient to provide costimulation. In control experiments, it was shown that the TC-1 response was alloantigen-specific since it was inhibited by an anti-DR mAb (described in R. I. Todd, et al. (1984) *Hum. Immunol.* 10:23 (1984) and since T cell proliferation or IL-2 accumulation was not induced by two other LBLs each homozygous for a different DR haplotype (LBL-DR1 and LBL-DR8).

EXAMPLE 3
Maintainence of T Cell Unresponsiveness by Blockage of a CD2/LFA-3 Interaction In a third series of experiment, the capacity of LBL-DR7 cells to restore alloantigen-specific responsiveness of TC-1 was investigated. The effect of LBL-DR7 was not mediated by a secreted soluble factor since rechallenge with t-DR7/B7-1 or t-DR7/ICAM-1 in the presence of LBL-DR7 culture supernatant did not restore responsiveness. In contrast, paraformaldehyde fixed, mitomycin-C treated, or irradiated LBL-DR7 cells induced identical proliferative response, suggesting that a cell surface molecule was involved in the observed reversal of anergy by LBL-DR7 cells. Blocking mAbs or fusion proteins directed against a variety of cell surface molecules expressed on APCs were used to determine whether a known cell surface molecule(s) was responsible for the restoration of responsiveness by LBL-DR7 cells. After anergy induction with t-DR7 allo-APCs, followed by culture in IL-2 for at least 7 days, TC-1 cells were rechallenged with LBL-DR7 either alone or in the presence of each one of the following mAbs or fusion proteins anti-DR (9-49) (described in R. I. Todd et al. (1984) *Hum. Immunol.* 10:23), anti-LFA-1 (TS1/22) (described in F. Sanchez-Madrid, et al. (1982) *Proc. Natl. Acad. Sci USA* 79:7489), anti-LFA-3 (TS29) (described in F. Sanchez-Madrid, et al. (1982) *Proc. Natl. Acad. Sci USA* 79:7489), anti-B7-1 (133) (described in A. S. Freedman, et al. (1987) *Immunol.* 137:3260), BB-1 (described in E. Clark et al in *Leukocyte Typing,* A. Bernard, et al., eds, (Springer-Verlang, Berlin Heidelberg, 1984, p. 339), CTLA4-Ig (described in C. D. Gimmi et al. (1993) *Proc. Natl. Acad. Sci USA* 90:6586), anti-CD24 (BA-1, 1:100 ascites) (described in C. S. Abramson, et al. (1981) *J. Immunol.* 126:83), anti-CD40 (JRG 12), anti-CD72 (J3-109, BU-40, 1:100 ascites) (described in B. Dorken, et al. *Leucocyte Typing IV White cell differentiation antigens,* W. Knapp et al, Eds (Oxford, 1989) p. 99). All (purified) mAbs and fusion proteins were used at 10 μg/ml. Proliferation was measured as in Example 1. Results are shown in FIG. 3 and are representative of four experiments.

Figure 3:
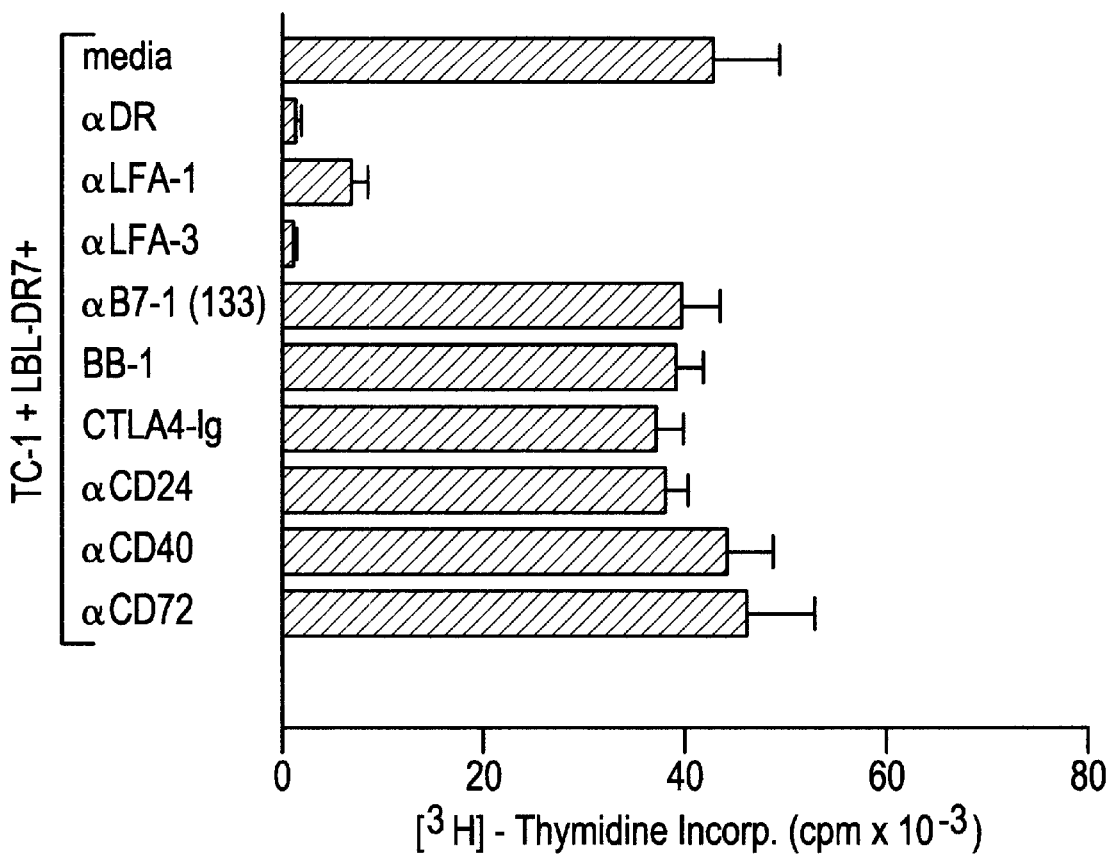
FIG. 3 is a bar graph depicting proliferation of anergized T cells following culture in IL-2 and stimulation by a lymphoblastoid cell line in the presence of antibodies directed against cell surface molecules on the lymphoblastoid cell line.

Only three mAbs inhibited the ability of LBL-DR7 to reverse T cell unresponsiveness (i.e., maintained T cell unresponsiveness): anti-DR, anti-LFA-1 and anti-LFA-3 (see FIG. 3). Neither B7 family members nor other cell surface molecules, including CD24, CD40, and CD72, appear to be important for the reversal of anergy, as evidenced by the inability of mAbs or fusion proteins which bind to these molecules to inhibit the proliferative response. The observed inhibition of LBL-DR7-mediated proliferation by anti-DR is due to inhibition of antigen recognition by the T cell. The observed inhibition of LBL-DR7-mediated proliferation by anti-LFA-3 is consistent with LFA-3 being involved in reversal of anergy, since T cell unresponsiveness is maintained when an interaction between LFA-3 on an antigen presenting cell and CD2 on an anergized T cell is inhibited (e.g., by blocking with an anti-LFA-3 antibody). The observed inhibition of LBL-DR7-mediated proliferation by anti-LFA-1 mAb suggests that LFA-1 ligands may also be involved in reversing anergy. It is unlikely that ICAM-1 is an LFA-3 ligand which is involved in reversing anergy, since t-DR7/ICAM-1 cells do not restore proliferation of anergized cells following prolonged IL-2 culture. However, other LFA-1 ligands, including ICAM-2 and ICAM-3, may also be involved in reversing anergy in addition to the CD2/LFA-3 interaction.

EXAMPLE 4
Reversal of T Cell Unresponsiveness by Stimulation with LFA-3

Figure 4:
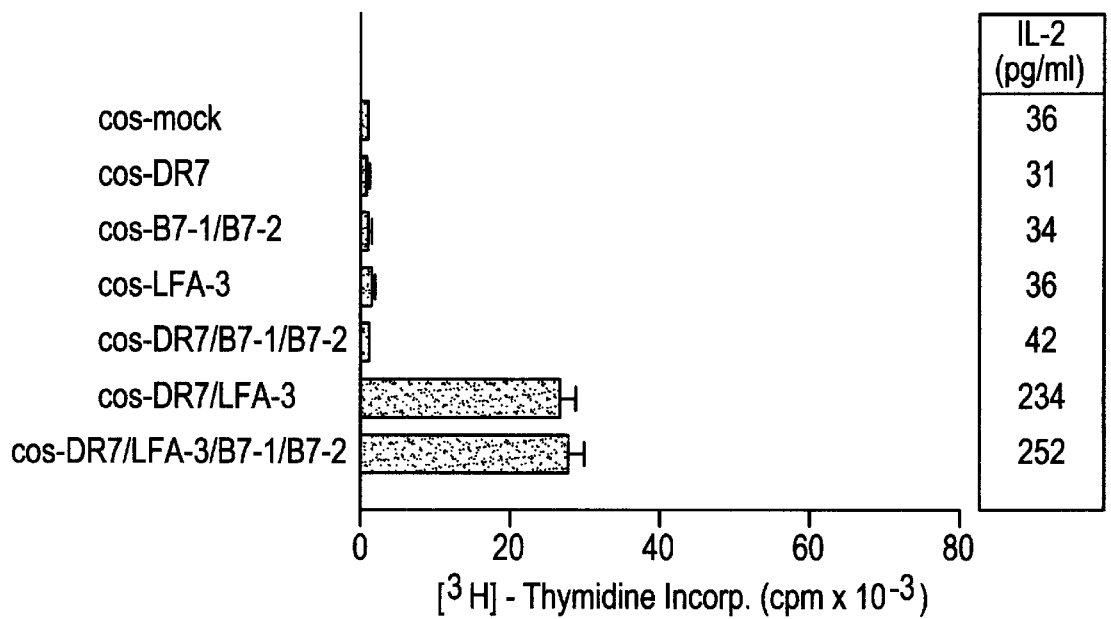
FIG. 4 is a bar graph depicting proliferation of and IL-2 production by anergized T cells following culture in IL-2 and stimulation by artificial antigen presenting cells.

To directly examine whether LFA-3 and alloantigen can reverse a state of established alloantigen-specific clonal anergy, COS cells were transfected to express DR7 alone (COS-DR7), B7-1 and B7-2 alone (COS-B7-1/B7-2) or LFA-3 alone (COS-LFA-3), or DR7 in combination with one or more of these molecules (COS-DR7/B7-1/B7-2, COS-DR7/LFA-3, COS-DR7/LFA-3/B7-1/B7-2). COS cells were transfected with cDNAs encoding either HLA-DRα and DR7β (DRB1*0701) chains (COS-DR7), B7-1 and B7-2 (COS-B7-1/B7-2), HLA-DRα and DR7β, B7-1 and B7-2 (COS-DR7/B7-1/B7-2), LFA-3 (COS-LFA-3), HLA-DRα and DR7β and LFA-3 (COS-DR7/LFA-3), HLA-DRα and DR7β, LFA-3, B7-1 and B7-2 (COS-DR7/LFA-3/B7-1/B7-2), or pCDNAI vector alone (COS-mock). The expression of DR7 and LFA-3 were assessed using 9-49 and TS2/9 mAb respectively, followed by FITC-conjugated goat anti-mouse Ig; the expression of B7-1 and B7-2 was assessed using biotinylated CTLA4-Ig, followed by phycoerythrin-conjugated streptavidin. The co-expression of LFA-3 and DR7 was assessed using TS2/9 followed by FITC-labeled goat anti-mouse Ig and phycoerythrin-conjugated 9-49, and was detectable in 50–72% of the transfected cells. The co-expression of DR7 and B7-1/B7-2 was assessed using FITC-conjugated 9-49 and biotinylated CTLA4-Ig, followed by phycoerythrin-conjugated streptavidin and was detectable in 40–50% of the transfected cells. Prior to use, transfected COS were treated with mitomycin-C as described in Example 1. After anergy induction with t-DR7 followed by culture in recombinant human IL-2, TC-1 cells ($2.5 \times 10^4$ cells/well) were rechallenged with $2 \times 10^4$ cells/well COS-transfectants of each type. Proliferation and IL-2 accumulation were measured as in Example 1. Results are shown in FIG. 4 and are representative of three experiments with COS-DR7/LFA-3, COS-DR7/B7-1/B7-2 and COS-mock, and two experiments with COS-DR7, COS-LFA-3, COS-B7-1/B7-2 and COS-DR7/LFA-3/B7-1/B7-2 transfectants. Challenge with COS-DR7, COS-B7-1/B7-2, COS-LFA-3, and COS-DR7/B7-1/B7-2 did not induce proliferation or IL-2 accumulation. In contrast, transfectants co-expressing DR7 and LFA-3 (COS-DR7/LFA-3, and COS-DR7/LFA-3/B7-1/B7-2) induced equivalent levels of proliferation and IL-2 accumulation indicating restored responsiveness to alloantigen in the presence of LFA-3 costimulation.

Figure 5:
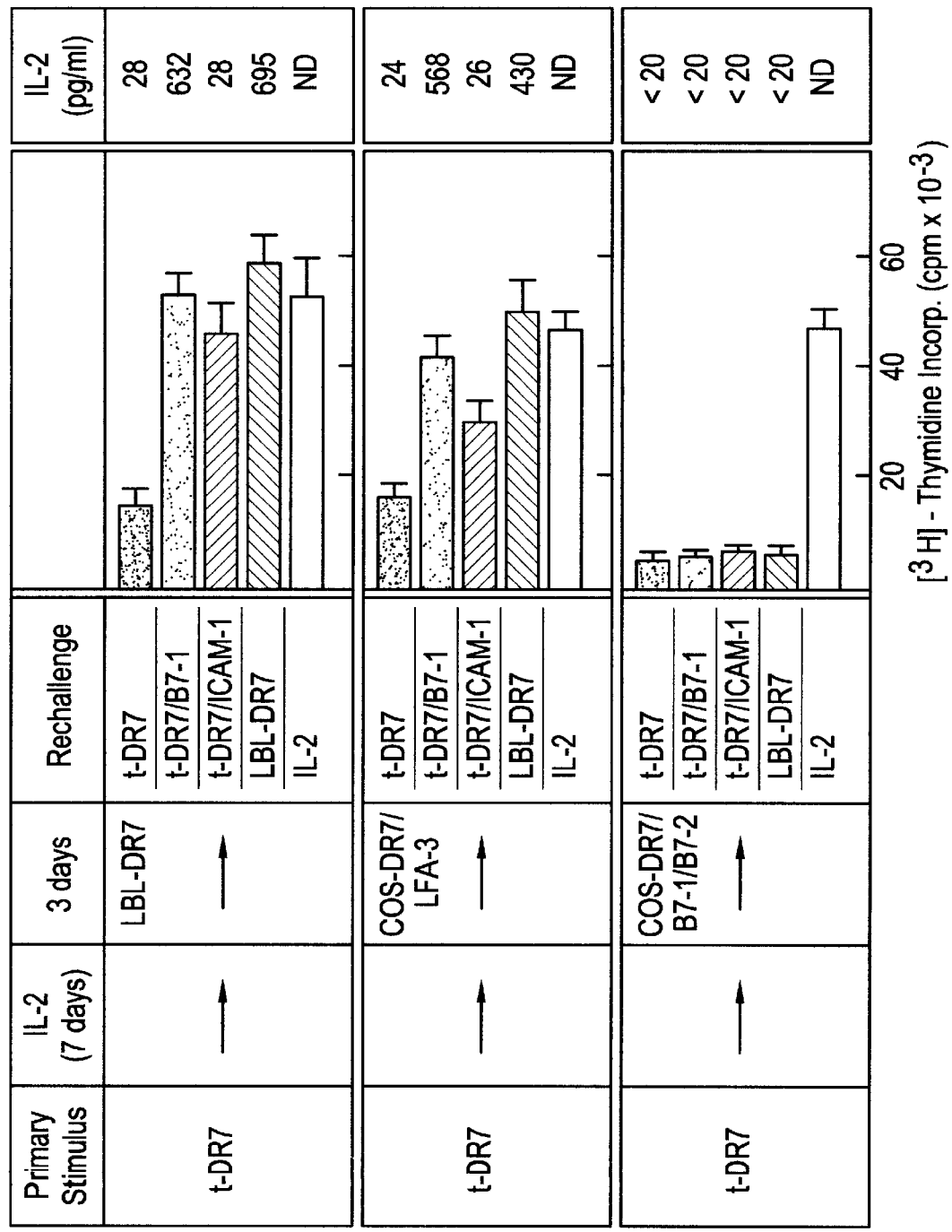
FIG. 5 is a series of bar graphs depicting T cell proliferation and IL-2 production following a primary stimulus, culture in IL-2, a second stimulus and rechallenge with artificial antigen presenting cells or a lymphoblastoid cell line.

To determine whether stimulation by LFA-3 reversed anergy and fully restored alloantigen-specific responsiveness, TC-1 cells were anergized, cultured in IL-2 and co-cultured with either LBL-DR7, COS-DR7/LFA-3 or COS-DR7/B7-1/B7-2 for 72 hours. Subsequently, they were isolated from LBL-DR7 by Ficoll separation and from COS transfectants by Percoll gradient centrifugation and rechallenged with the indicated stimuli. Results shown in FIG. 5 are representative of five experiments when rechallenge was done with LBL-DR7 stimulators and three experiments when rechallenge was done with COS transfectants as stimulators. Following sequential culture with IL-2 and LBL-DR7 or COS-DR7/LFA-3, previously anergized TC-1 cells respond to t-DR7/B7-1, t-DR7/ICAM-1, and LBL-DR7 (see FIG. 5, upper and middle panels). In contrast, when COS-DR7/B7-1/B7-2 were used following IL-2 culture, no response on rechallenge was seen (FIG. 5, lower panel). In all instances, TC-1 cells proliferate equally to exogenous IL-2 (FIG. 5). This demonstrates that culture of anergized TC-1 in IL-2 for at least 7 days, followed by presentation of alloantigen and stimulation by LFA-3, is sufficient to reverse alloantigen-specific anergy and restore responsiveness to alloantigen in the presence of previously insufficient costimulatory signals.

EXAMPLE 5
Re-expression of the CD2 Neo-Epitope T11.3 on an Anergized T Cell by Culture in IL-2

Figure 6:
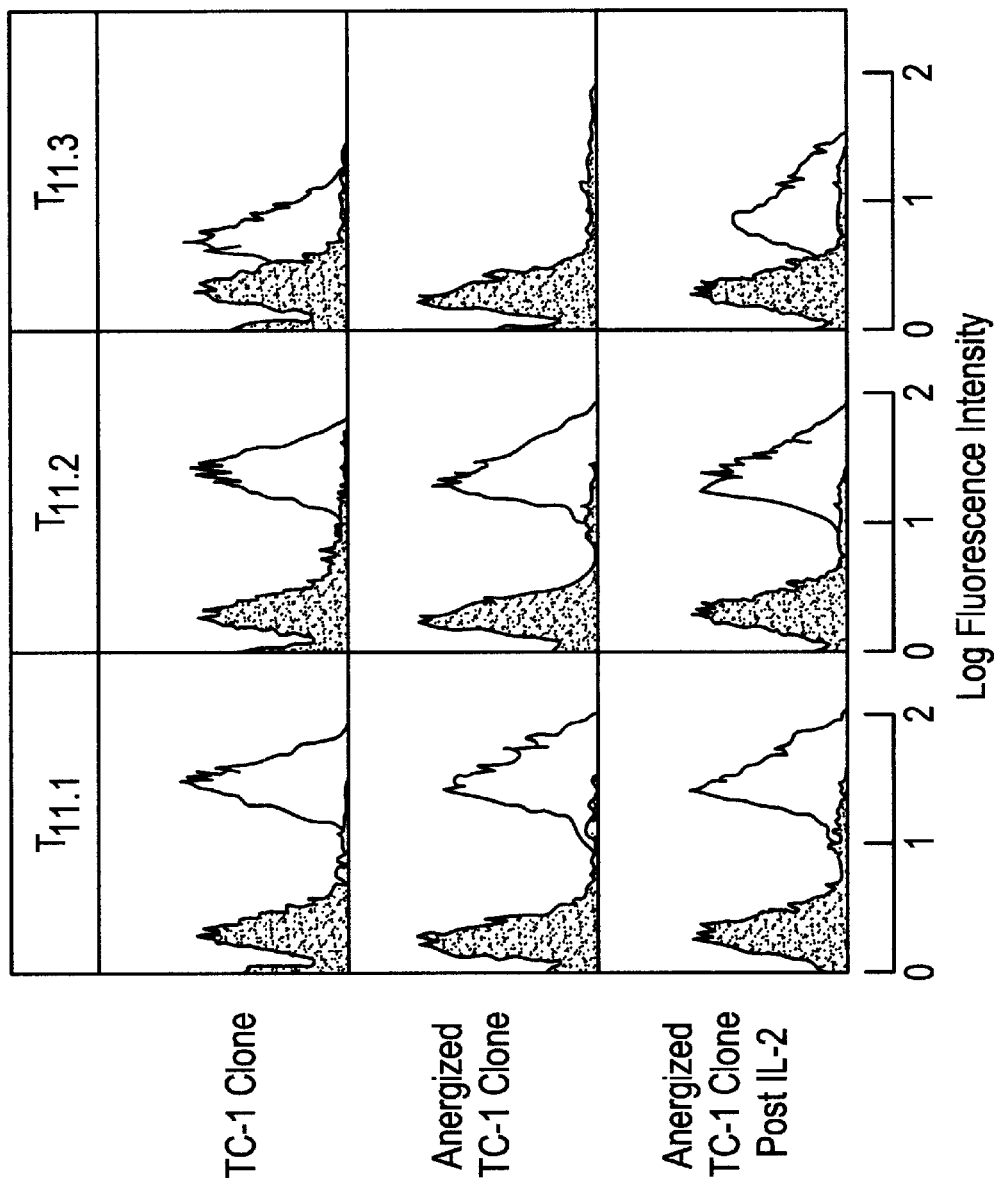
FIG. 6 is a series of graphs depicting the expression of the CD2 epitopes T11.1, T11.2 and T11.3 on TC-1 cells, anergized TC-1 cells and anergized TC-1 cells following culture in IL-2.

The expression of the CD2 epitopes T11.1 and T11.2 (CD2), and T11.3 (CD2R) by TC-1 was examined by flow cytometry under various culture conditions. TC-1 cells before and after induction of anergy and following culture with IL-2 for 7 days were stained with antibodies for the T11.1, T11.2, or T11.3 epitopes of the CD2 molecule or the appropriate isotype matched controls and were analyzed by flow cytometric analysis (EPICS Elite Flow cytometer; Coulter). The results are shown in FIG. 6. The shaded peaks represent staining with isotype matched mAb and the unshaded peaks represent staining with mAbs for either T11.1, T11.2 or T11.3 epitopes, as indicated. Data are representative of three experiments. In a responsive state, TC-1 cells express T11.1, T11.2 and T11.3 epitopes. Following induction of anergy in TC-1 by culture with t-DR7 (as described in Example 1), TC-1 cells still express T11.1 and T11.2 but expression of T11.3 (CD2R) is no longer detectable. The T11.3 epitope is re-expressed after 7 days of culture with IL-2, precisely when these cells regain responsiveness to alloantigen and LFA-3 costimulation (see FIG. 6). Moreover, although non-anergic TC-1 cells proliferate to the mitogenic combination of T11.3 with ether T11.1 or T11.2 mAbs, anergized TC-1 cells do not. Following 7 days of IL-2 culture and accompanying the reappearance of the T11.3 epitope, anergic TC-1 cells regain responsiveness to mitogenic combinations of anti-CD2 mAbs (e.g., T11.3 with either T11.1 or T11.2 mAbs). The absence of detectable T11.3 epitope on TC-1 cells following induction of anergy was not due simply to a lack of T cell proliferation but was directly related to the induction of anergy.

EXAMPLE 6

Association of CD2 with JAK-3 Kinase Upon Reversal of T Cell Anergy

Figure 7B:
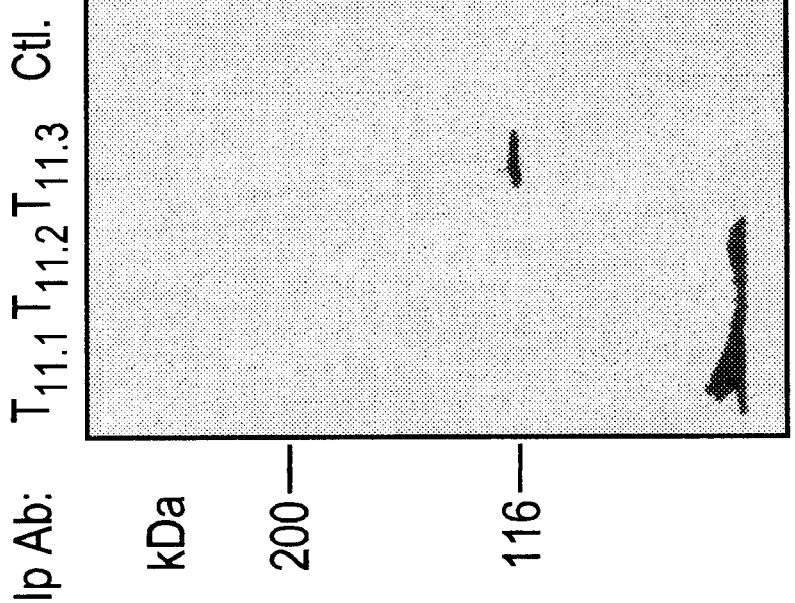
FIG. 7 is a photograph of an immunoblot filter of T cell proteins immuno-precipitated with an anti-CD2 antibody (T11.1, T11.2 or T11.3) and immunoblotted with a JAK kinase-specific antiserum (R80)(left panel) or a JAK-3 kinase-specific antiserum (right panel), depicting association of the T11.3-expressing form of CD2 with JAK-3 kinase.
Figure 7A:
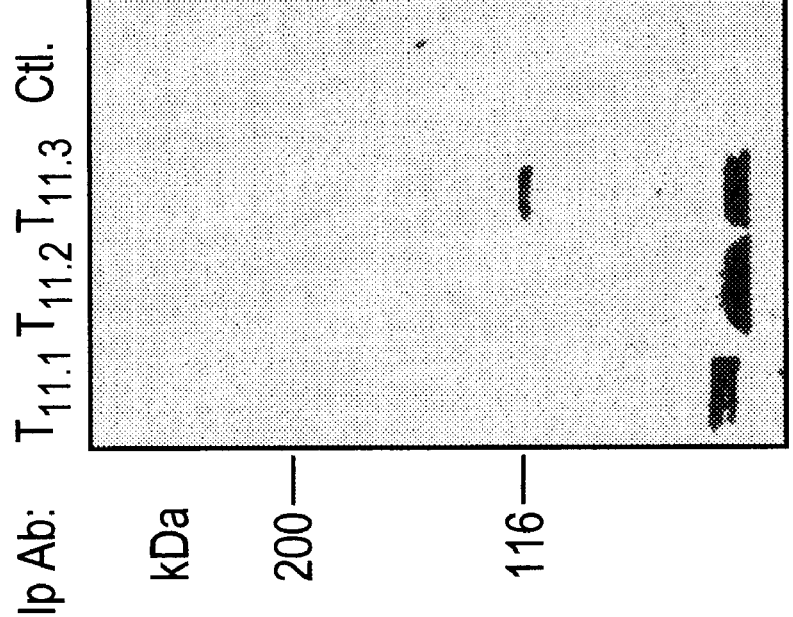

Stimulation of non-anergized TC-1 cells with either t-DR7/B7-1 or LBL-DR7 cells resulted in tyrosine phosphorylation of the tyrosine kinases JAK-1 and JAK-3. To examine the role of JAK kinases in reversal of T cell anergy, previously anergized TC-1 cells were challenged with various stimulatory agents and then JAK kinase phosphorylation and association with CD2 was examined. In contrast to non-anergized T cells, previously anergized T cells did not exhibit tyrosine phosphorylation of either JAK-1 or JAK-3 kinase when challenged with either t-DR7/B7-1 or LBL-DR7. However, after 7 days of culture of the T cells in IL-2, rechallenge of the cells with LBL-DR7 resulted in significant phosphorylation of JAK-1 and JAK-3 kinases. This time period following IL-2 culture coincides with the time when the T cells regain responsiveness to alloantigen and LFA-3 stimulation. To determine whether CD2 was associated with any of the JAK kinase family members at this time, TC-1 cell lysates were immunoprecipitated with a monoclonal antibody against CD2, either T11.1, T11.2 or T11.3, and the immunoprecipitates cell were electrophoresed on a standard SDS-PAGE gel. The proteins on the gel were transferred to a filter, which was then immunoblotted with a common anti-JAK kinase antiserum (R80) or a JAK-3-specific antiserum. The results of these immunoblot experiments are shown in FIG. 7. These experiments demonstrated that, upon reversal of T cell anergy, the T11.3-expressing form of CD2 was associated with a 116 kD JAK kinase (see FIG. 7, left panel). Furthermore, this 116 kD JAK kinase was identified as JAK-3 kinase upon immunblotting of with an antiserum specific for JAK-3 kinase (see FIG. 7, right panel).

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for stimulating a T cell response to a tumor cell in a subject with a rumor, comprising modifying the tumor cell to express LFA-3 and a CD28 or CTLA4 ligand wherein said CD28 or CTLA4 ligand is selected from the group consisting of B7-1, B7-2, and combinations Thereof, such that stimulation of a T cell response to a tumor cell occurs.

2. The method of claim 1, wherein the tumor cell is modified to express LFA-3 and the CD28 or CTLA4 ligand by introducing into the tumor cell at least one nucleic acid encoding LFA-3 and the CD28 or CTLA4 ligand in a form suitable for expression of LFA-3 and the CD28 or CTLA4 ligand on the tumor cell surface.

3. The method of claim 1, wherein the tumor cell is obtained from the subject and modified ex vivo to form a modified tumor cell and the method further comprises administering the modified tumor cell to the subject.

4. The method of claim 1, wherein a first sample of tumor cells is modified to express LFA-3 to form a first sample of modified tumor cells and a second sample of tumor cells is modified to express the CD28 or CTLA4 ligand to form a second sample of modified tumor cells.

5. The method of claim 4, wherein the first and second samples of modified tumor cells are administered to the subject simultaneously.

6. The method of claim 4, wherein the first and second samples of modified tumor cells are administered to the subject sequentially.

7. The method of claim 1, further comprising contacting T cells of the subject with an agent that stimulates exposure of a T11.3 neo-epitope on a CD2 surface receptor on the T cell.

8. The method of claim 7, wherein the agent is IL-2 or IL-4.

9. The method of claim 8, wherein the T cells are obtained from the subject and contacted with IL-2 or IL-4 ex vivo and the method further comprises readministering the T cells to the subject.

10. The method of claim 1, wherein the CD28 or CTLA4 ligand is B7-1.

11. The method of claim 1, wherein the CD28 or CTLA4 ligand is B7-2.

12. The method of claim 1, wherein the CD28 or CTLA4 ligand is B7-1 and B7-2.

* * * * *

UNITED STATES PATENT AND TRADEMARK OFFICE
CERTIFICATE OF CORRECTION

PATENT NO.      : 6,451,305 B1
DATED           : September 17, 2002
INVENTOR(S)     : Vassiliki A. Boussiotis et al.

It is certified that error appears in the above-identified patent and that said Letters Patent is hereby corrected as shown below:

Column 26,
Line 14, "rumour" should be -- tumor --
Line 17, "Thereof" should be -- thereof --

Signed and Sealed this

Eighteenth Day of February, 2003

JAMES E. ROGAN
*Director of the United States Patent and Trademark Office*